(12) United States Patent
Selby et al.

(10) Patent No.: US 11,266,774 B2
(45) Date of Patent: Mar. 8, 2022

(54) FLUID COLLECTION APPARATUS

(71) Applicant: ConvaTec Technologies Inc., Las Vegas, NV (US)

(72) Inventors: Robert Gordon Maurice Selby, Royston (GB); Lawrence Mark Baker, Royston (GB); Steven Paul Gowers, Royston (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 267 days.

(21) Appl. No.: 16/315,999

(22) PCT Filed: Jul. 7, 2017

(86) PCT No.: PCT/US2017/041208
§ 371 (c)(1),
(2) Date: Jan. 7, 2019

(87) PCT Pub. No.: WO2018/009873
PCT Pub. Date: Jan. 11, 2018

(65) Prior Publication Data
US 2019/0298895 A1 Oct. 3, 2019

Related U.S. Application Data

(60) Provisional application No. 62/360,211, filed on Jul. 8, 2016.

(51) Int. Cl.
*A61M 1/00* (2006.01)
(52) U.S. Cl.
CPC .............. *A61M 1/602* (2021.05); *A61M 1/88* (2021.05); *A61M 1/90* (2021.05)

(58) Field of Classification Search
CPC .............. A61M 1/0015; A61M 1/0094; A61M 1/0088; A61M 2206/10; A61M 1/0017;
(Continued)

(56) References Cited

U.S. PATENT DOCUMENTS

| 4,441,215 A | 4/1984 | Kaster |
| 5,358,492 A | 10/1994 | Feibus |

(Continued)

FOREIGN PATENT DOCUMENTS

| EP | 1905465 A1 * | 4/2008 | .......... A61M 1/0015 |
| EP | 2711034 A1 | 3/2014 | |

(Continued)

OTHER PUBLICATIONS

French to English machine translation of FR-2939320.*
(Continued)

*Primary Examiner* — Nicholas J Weiss
*Assistant Examiner* — Gregory J Feulner
(74) *Attorney, Agent, or Firm* — Taft Stettinius & Hollister LLP; Ryan O. White; Derek B. Lavender

(57) ABSTRACT

A fluid collection apparatus for use in negative pressure wound therapy. The fluid collection apparatus includes a flexible bag having a first opening and a second opening. The bag includes a structure defining a fluid pathway connecting the first opening and the second opening. The pathway is circulative and contributes to orientation independence of the bag in use. The bag further includes a load-bearing component.

20 Claims, 7 Drawing Sheets

(58) Field of Classification Search
CPC ............ A61M 1/009; A61M 13/00068; A61M 13/0216; A61M 1/0023
See application file for complete search history.

(56) References Cited

U.S. PATENT DOCUMENTS

| | | | |
|---|---|---|---|
| 6,695,823 B1 | 2/2004 | Lina et al. | |
| 8,034,038 B2 * | 10/2011 | Biggie | A61M 27/00 604/319 |
| 8,083,712 B2 | 12/2011 | Biggie et al. | |
| 8,308,714 B2 | 11/2012 | Weston et al. | |
| 8,439,894 B1 | 5/2013 | Miller | |
| 8,521,979 B2 | 8/2013 | Laberge et al. | |
| 8,814,840 B2 | 8/2014 | Evans et al. | |
| 8,858,516 B2 * | 10/2014 | Hu | A61M 1/0068 604/290 |
| 9,180,231 B2 * | 11/2015 | Greener | A61M 1/0031 |
| 9,205,183 B2 | 12/2015 | Hartwell et al. | |
| 9,433,712 B2 | 9/2016 | Locke et al. | |
| 9,622,907 B2 * | 4/2017 | Carson | A61F 7/10 |
| 9,687,386 B2 * | 6/2017 | Carson | A61F 7/10 |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,143,784 B2 | 12/2018 | Walton et al. | |
| 10,426,670 B2 | 10/2019 | von Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,441,458 B2 * | 10/2019 | Voorhees | A61F 7/10 |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |
| 10,485,707 B2 | 11/2019 | Sexton | |
| 10,485,891 B2 | 11/2019 | Andrews et al. | |
| 10,485,892 B2 | 11/2019 | Hands et al. | |
| 10,485,906 B2 | 11/2019 | Freedman et al. | |
| 10,486,135 B2 | 11/2019 | Yang et al. | |
| 10,492,956 B2 | 12/2019 | Zamierowski | |
| 10,493,178 B2 | 12/2019 | Marchant et al. | |
| 10,493,184 B2 | 12/2019 | Collinson et al. | |
| 10,493,185 B2 | 12/2019 | Stokes et al. | |
| 10,500,099 B2 | 12/2019 | Hung et al. | |
| 10,500,103 B2 | 12/2019 | Croizat et al. | |
| 10,500,104 B2 | 12/2019 | Sookraj | |
| 10,500,173 B2 | 12/2019 | Yang et al. | |
| 10,500,235 B2 | 12/2019 | Wardell | |
| 10,500,300 B2 | 12/2019 | Dybe et al. | |
| 10,500,301 B2 | 12/2019 | Laurensou | |
| 10,500,302 B2 | 12/2019 | Holm et al. | |
| 10,501,487 B2 | 12/2019 | Andrews et al. | |
| 10,506,928 B2 | 12/2019 | Locke et al. | |
| 10,507,141 B2 | 12/2019 | Allen et al. | |
| 10,507,259 B2 | 12/2019 | Cree et al. | |
| 10,512,707 B2 | 12/2019 | Whalen, III et al. | |
| 10,525,170 B2 | 1/2020 | Havenstrite et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,548,777 B2 | 2/2020 | Locke et al. | |
| 10,549,008 B2 | 2/2020 | Yoo | |
| 10,549,016 B2 | 2/2020 | Bushko et al. | |
| 10,549,017 B2 | 2/2020 | Hsiao et al. | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,533 B2 | 2/2020 | Hoggarth et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,770 B2 | 2/2020 | Robinson et al. | |
| 10,568,771 B2 | 2/2020 | MacDonald et al. | |
| 10,568,773 B2 | 2/2020 | Tuck et al. | |
| 10,568,983 B2 | 2/2020 | Gerdes et al. | |
| 10,575,991 B2 | 3/2020 | Dunn | |
| 10,575,992 B2 | 3/2020 | Sarangapani et al. | |
| 10,576,037 B2 | 3/2020 | Harrell | |
| 10,576,189 B2 | 3/2020 | Locke et al. | |
| 10,583,042 B2 | 3/2020 | Sarangapani et al. | |
| 10,583,228 B2 | 3/2020 | Shuler et al. | |
| 10,589,007 B2 | 3/2020 | Coulthard et al. | |
| 10,590,184 B2 | 3/2020 | Kuo | |
| 10,610,414 B2 | 4/2020 | Hartwell et al. | |
| 10,610,415 B2 | 4/2020 | Griffey et al. | |
| 10,610,623 B2 | 4/2020 | Robinson et al. | |
| 10,617,569 B2 | 4/2020 | Bonn | |
| 10,617,608 B2 | 4/2020 | Shin et al. | |
| 10,617,769 B2 | 4/2020 | Huang | |
| 10,617,784 B2 | 4/2020 | Yu et al. | |
| 10,617,786 B2 | 4/2020 | Kluge et al. | |
| 10,618,266 B2 | 4/2020 | Wright et al. | |
| 10,624,984 B2 | 4/2020 | Courage et al. | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,350 B2 | 5/2020 | Arber et al. | |
| 10,639,404 B2 | 5/2020 | Lichtenstein | |
| 10,646,614 B2 | 5/2020 | Grinstaff et al. | |
| 10,653,562 B2 | 5/2020 | Robinson et al. | |
| 10,653,782 B2 | 5/2020 | Ameer et al. | |
| 10,653,810 B2 | 5/2020 | Datt et al. | |
| 10,653,821 B2 | 5/2020 | Nichols | |
| 10,653,823 B2 | 5/2020 | Bharti et al. | |
| 10,660,799 B2 | 5/2020 | Wu et al. | |
| 10,660,851 B2 | 5/2020 | Millis et al. | |
| 10,660,992 B2 | 5/2020 | Canner et al. | |
| 10,660,994 B2 | 5/2020 | Askem et al. | |
| 10,667,955 B2 | 6/2020 | Allen et al. | |
| 10,667,956 B2 | 6/2020 | Van Holten et al. | |
| 10,682,257 B2 | 6/2020 | Lu | |
| 10,682,258 B2 | 6/2020 | Manwaring et al. | |
| 10,682,259 B2 | 6/2020 | Hunt et al. | |
| 10,682,318 B2 | 6/2020 | Twomey et al. | |
| 10,682,386 B2 | 6/2020 | Ellis-Behnke et al. | |
| 10,682,446 B2 | 6/2020 | Askem et al. | |
| 10,687,983 B2 | 6/2020 | Dahlberg et al. | |
| 10,687,985 B2 | 6/2020 | Lee et al. | |
| 10,688,215 B2 | 6/2020 | Munro et al. | |
| 10,688,217 B2 | 6/2020 | Hanson et al. | |
| RE48,117 E | 7/2020 | Albert et al. | |
| 10,702,419 B2 | 7/2020 | Locke et al. | |
| 10,702,420 B2 | 7/2020 | Hammond et al. | |
| 10,703,942 B2 | 7/2020 | Tunius | |
| 10,709,760 B2 | 7/2020 | Gronberg et al. | |
| 10,709,807 B2 | 7/2020 | Kshirsagar | |
| 10,709,883 B2 | 7/2020 | Spector | |
| 10,716,711 B2 | 7/2020 | Locke et al. | |
| 10,716,874 B2 | 7/2020 | Koyama et al. | |
| 10,729,589 B2 | 8/2020 | Dorian et al. | |
| 10,729,590 B2 | 8/2020 | Simmons et al. | |
| 10,729,826 B2 | 8/2020 | Lin | |
| 10,736,787 B2 | 8/2020 | Hannigan et al. | |
| 10,736,788 B2 | 8/2020 | Locke et al. | |
| 10,736,985 B2 | 8/2020 | Odermatt et al. | |
| 10,737,003 B2 | 8/2020 | Fujisaki | |
| 10,743,900 B2 | 8/2020 | Ingram et al. | |

(56) References Cited

U.S. PATENT DOCUMENTS

| | | | |
|---|---|---|---|
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2006/0155260 A1* | 7/2006 | Blott ............ A61M 1/0084 604/543 |
| 2006/0172000 A1 | 8/2006 | Cullen et al. |
| 2007/0185426 A1 | 8/2007 | Ambrosio et al. |
| 2007/0208300 A1 | 9/2007 | Pravong et al. |
| 2007/0219512 A1 | 9/2007 | Heaton et al. |
| 2007/0239078 A1 | 10/2007 | Jaeb |
| 2007/0265586 A1* | 11/2007 | Joshi ............ A61F 13/0216 604/313 |
| 2009/0082731 A1 | 3/2009 | Moreno |
| 2009/0204085 A1* | 8/2009 | Biggie ............ A61M 27/00 604/313 |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0036333 A1 | 2/2010 | Schenk, III et al. |
| 2010/0069863 A1 | 3/2010 | Olson |
| 2010/0125233 A1 | 5/2010 | Edward et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2010/0318043 A1 | 12/2010 | Malhi et al. |
| 2010/0324516 A1 | 12/2010 | Braga et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0152799 A1 | 6/2011 | Kevin et al. |
| 2011/0172616 A1 | 7/2011 | Hartwell et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0276016 A1 | 11/2011 | Tsai |
| 2012/0016322 A1 | 1/2012 | Coulthard et al. |
| 2012/0065602 A1 | 3/2012 | Adams et al. |
| 2012/0071845 A1 | 3/2012 | Hu et al. |
| 2012/0100538 A1 | 4/2012 | Mikolajczyk et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0096518 A1* | 4/2013 | Hall ............ A61F 13/00068 604/319 |
| 2013/0116760 A1* | 5/2013 | Carson ............ A61F 7/10 607/104 |
| 2013/0123728 A1 | 5/2013 | Pratt et al. |
| 2013/0226063 A1 | 8/2013 | Taylor et al. |
| 2013/0267918 A1 | 10/2013 | Pan et al. |
| 2013/0296816 A1 | 11/2013 | Greener |
| 2014/0005618 A1 | 1/2014 | Locke et al. |
| 2014/0031771 A1 | 1/2014 | Locke et al. |
| 2014/0074053 A1 | 3/2014 | Locke et al. |
| 2014/0107599 A1 | 4/2014 | Fink et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276489 A1 | 9/2014 | Robinson et al. |
| 2014/0276499 A1* | 9/2014 | Locke ............ A61F 13/0216 604/322 |
| 2014/0296804 A1 | 10/2014 | Hicks et al. |
| 2014/0308338 A1 | 10/2014 | Nierle et al. |
| 2014/0309574 A1 | 10/2014 | Cotton |
| 2014/0336602 A1 | 11/2014 | Karpowicz et al. |
| 2014/0343519 A1* | 11/2014 | Weston ............ A61M 1/0066 604/319 |
| 2015/0018433 A1 | 1/2015 | Leipzig et al. |
| 2015/0057624 A1 | 2/2015 | Simmons et al. |
| 2015/0057625 A1 | 2/2015 | Coulthard |
| 2015/0071985 A1 | 3/2015 | Walker et al. |
| 2015/0073359 A1* | 3/2015 | Hudspeth ............ A61M 1/0033 604/315 |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0182677 A1 | 7/2015 | Collinson et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0290364 A1 | 10/2015 | Wall et al. |
| 2015/0320901 A1 | 11/2015 | Chandrashekhar-Bhat et al. |
| 2015/0351970 A1 | 12/2015 | Dagger et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0144084 A1* | 5/2016 | Collinson ............ A61M 1/0088 |
| 2016/0151547 A1 | 6/2016 | Hartwell et al. |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0152076 A1* | 6/2017 | Sybouts ............ B65D 33/01 |
| 2017/0189237 A1 | 7/2017 | Locke et al. |

(56) References Cited

U.S. PATENT DOCUMENTS

| | | |
|---|---|---|
| 2017/0189575 A1 | 7/2017 | Lee et al. |
| 2017/0209615 A1 | 7/2017 | Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0060532 A1 | 2/2019 | Hartwell et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |

(56) References Cited

U.S. PATENT DOCUMENTS

| | | |
|---|---|---|
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |

(56) References Cited

U.S. PATENT DOCUMENTS

| | | |
|---|---|---|
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | | |
|---|---|---|---|
| EP | 2817038 A1 | 12/2014 | |
| EP | 3187204 A1 | 7/2017 | |
| EP | 3643328 A1 | 4/2020 | |
| EP | 3643330 A1 | 4/2020 | |
| EP | 3643331 A1 | 4/2020 | |
| EP | 3669838 A1 | 6/2020 | |
| EP | 3669843 A1 | 6/2020 | |
| EP | 3669844 A1 | 6/2020 | |
| FR | 2939320 A1 * | 6/2010 | .......... A61M 1/0072 |
| GB | 2579211 A | 6/2020 | |
| GB | 2579368 A | 6/2020 | |
| JP | 200880137 A | 4/2008 | |
| JP | 2015144859 A | 8/2015 | |
| JP | 2015532847 A | 11/2015 | |
| WO | 2005018543 A2 | 3/2005 | |
| WO | WO 2007030599 * | 3/2007 | ....... A61F 13/00063 |
| WO | WO-2009071938 A1 * | 6/2009 | .......... A61M 35/006 |
| WO | WO-2009106895 A1 | 9/2009 | |
| WO | 2010056977 A2 | 5/2010 | |
| WO | 2011121394 A1 | 10/2011 | |
| WO | 2011135284 A1 | 11/2011 | |
| WO | 2011144888 A1 | 11/2011 | |
| WO | WO-2012057881 A1 | 5/2012 | |
| WO | 2013015827 A2 | 1/2013 | |
| WO | 2013039623 A1 | 3/2013 | |
| WO | WO 2013/06694 A3 * | 5/2013 | .......... A61M 3/0279 |
| WO | 2013126049 A1 | 8/2013 | |
| WO | 2014014842 A1 | 1/2014 | |
| WO | 2014045047 A1 | 3/2014 | |
| WO | WO-2015052219 A1 | 4/2015 | |
| WO | 2015145117 A1 | 10/2015 | |
| WO | 2015173546 A1 | 11/2015 | |
| WO | 2016141450 A1 | 9/2016 | |
| WO | 2017016974 A1 | 2/2017 | |
| WO | WO-2017068364 A1 | 4/2017 | |
| WO | 2017125250 A1 | 7/2017 | |
| WO | WO-2017196888 A1 | 11/2017 | |
| WO | WO-2018009873 A1 | 1/2018 | |
| WO | WO-2018009879 A1 | 1/2018 | |
| WO | WO-2018009880 A1 | 1/2018 | |
| WO | 2018029231 A1 | 2/2018 | |
| WO | 2018094061 A1 | 5/2018 | |
| WO | 2018162613 A1 | 9/2018 | |
| WO | 2018163093 A1 | 9/2018 | |
| WO | 2018189265 A1 | 10/2018 | |
| WO | 2018226667 A1 | 12/2018 | |
| WO | 2018227144 A1 | 12/2018 | |
| WO | 2018231825 A1 | 12/2018 | |
| WO | 2018236648 A1 | 12/2018 | |
| WO | 2019002085 A1 | 1/2019 | |
| WO | 2019012068 A1 | 1/2019 | |
| WO | 2019012069 A1 | 1/2019 | |
| WO | 2019022493 A1 | 1/2019 | |
| WO | 2019027933 A1 | 2/2019 | |
| WO | 2019038548 A1 | 2/2019 | |
| WO | 2019038549 A1 | 2/2019 | |
| WO | 2019040656 A1 | 2/2019 | |
| WO | 2019050855 A1 | 3/2019 | |
| WO | 2019058373 A1 | 3/2019 | |
| WO | 2019073326 A1 | 4/2019 | |
| WO | 2019083563 A1 | 5/2019 | |
| WO | 2019083868 A1 | 5/2019 | |
| WO | 2019086911 A1 | 5/2019 | |
| WO | 2019091150 A1 | 5/2019 | |
| WO | 2019094147 A1 | 5/2019 | |
| WO | 2019096828 A1 | 5/2019 | |
| WO | 2019113275 A1 | 6/2019 | |
| WO | 2019113623 A1 | 6/2019 | |
| WO | 2019191590 A1 | 10/2019 | |
| WO | 2019193141 A1 | 10/2019 | |
| WO | 2019193333 A1 | 10/2019 | |
| WO | 2019199389 A1 | 10/2019 | |
| WO | 2019199596 A1 | 10/2019 | |
| WO | 2019199687 A1 | 10/2019 | |
| WO | 2019199798 A1 | 10/2019 | |
| WO | 2019199849 A1 | 10/2019 | |
| WO | 2019200035 A1 | 10/2019 | |
| WO | 2019215572 A1 | 11/2019 | |
| WO | 2019219613 A1 | 11/2019 | |
| WO | 2019234365 A1 | 12/2019 | |
| WO | 2020005062 A1 | 1/2020 | |
| WO | 2020005344 A1 | 1/2020 | |
| WO | 2020005536 A1 | 1/2020 | |
| WO | 2020005546 A1 | 1/2020 | |
| WO | 2020005577 A1 | 1/2020 | |
| WO | 2020007429 A1 | 1/2020 | |
| WO | 2020011691 A1 | 1/2020 | |
| WO | 2020014178 A1 | 1/2020 | |
| WO | 2020014310 A1 | 1/2020 | |
| WO | 2020018300 A1 | 1/2020 | |
| WO | 2020026061 A1 | 2/2020 | |
| WO | 2020026144 A1 | 2/2020 | |
| WO | 2020033351 A1 | 2/2020 | |
| WO | 2020035811 A1 | 2/2020 | |
| WO | 2020043665 A1 | 3/2020 | |
| WO | 2020044237 A1 | 3/2020 | |
| WO | 2020046443 A1 | 3/2020 | |
| WO | 2020047255 A1 | 3/2020 | |
| WO | 2020049038 A1 | 3/2020 | |
| WO | 2020055945 A1 | 3/2020 | |
| WO | 2020056014 A1 | 3/2020 | |
| WO | 2020056182 A1 | 3/2020 | |
| WO | 2020065531 A1 | 4/2020 | |
| WO | 2020070231 A1 | 4/2020 | |
| WO | 2020074512 A1 | 4/2020 | |
| WO | 2020078993 A1 | 4/2020 | |
| WO | 2020079009 A1 | 4/2020 | |
| WO | 2020079330 A1 | 4/2020 | |
| WO | 2020081259 A1 | 4/2020 | |
| WO | 2020081391 A1 | 4/2020 | |
| WO | 2020092598 A1 | 5/2020 | |
| WO | 2020136555 A1 | 7/2020 | |
| WO | 2020141059 A1 | 7/2020 | |

OTHER PUBLICATIONS

M. Patziger. Computational fluid dynamics investigation of shallow circular secondary settling tanks: Inlet geometry and performance indicators. Chemical Engineering Research and Design 112 (2016) 122-131. Available on line Jun. 23, 2016.*

M. Patziger, "Computational fluid dynamics investigation of shallow circular secondary settling tanks: Inlet geometry and performance" Chemical Engineering Research and Design 112 (2016) 122-131.*

Definition of Weld, https://www.merriam-webster.com/dictionary/weld Accessed Jun. 30, 2021.*

Colombian Application No. NC2018/0005230 Office Action dated May 31, 2018.

Great Britain Application No. GB1608099.6 search report dated Oct. 11, 2016.

PCT/US2017/041221 International Search Report and Written Opinion dated Sep. 13, 2017.

PCT/GB2016/053295 International Preliminary Report on Patentability dated Apr. 24, 2018.

PCT/GB2016/053295 International Search Report and Written Opinion dated Jan. 17, 2017.

(56) References Cited

OTHER PUBLICATIONS

PCT/US2017/031817 International Search Report and Written Opinion dated Aug. 11, 2017.
PCT/US2017/031817 International Preliminary Report on Patentability dated Nov. 13, 2018.
PCT/US2017/041208 International Search Report and Written Opinion dated Sep. 8, 2017.
PCT/US2017/041216 International Search Report and Written Opinion dated Sep. 13, 2017.
PCT/US2017/041208 International Preliminary Report on Patentability dated Jan. 8, 2019.
PCT/US2017/041216 International Preliminary Report on Patentability dated Jan. 8, 2019.
PCT/US2017/041221 International Preliminary Report on Patentability dated Jan. 8, 2019.
Examination Report No. 1; Australian Government IP Australia; Patent Application No. 2017292876; dated Nov. 18, 2021; 5 pages.

* cited by examiner

FLUID COLLECTION APPARATUS

CROSS-REFERENCE

This application is a U.S. National Phase of International Application No. PCT/US2017/041208, filed on Jul. 7, 2017, which claims the benefit of U.S. Provisional Application No. 62/360,211, filed Jul. 8, 2016, both of which are incorporated herein by reference in their entirety.

BACKGROUND OF THE INVENTION

Open wounds may be treated by providing negative pressure to the space above the wound to promote healing in a process often referred to a negative pressure wound therapy (NPWT). During NPWT, effluent such as exudates are removed from the wound and collected. In some therapies, the effluent is stored in a fluid collection apparatus, or canister, positioned between the source of negative pressure and a cover providing the space above the wound. Typically the canister has a stiffness that supports the structure of the canister during application of negative pressure.

SUMMARY OF THE INVENTION

In one aspect, provided herein is a fluid collection apparatus for negative pressure wound therapy comprising a flexible bag having a first opening and a second opening; wherein the bag comprises (a) a structure defining a fluid pathway connecting the first opening and the second opening; and (b) a load-bearing component. In some embodiments, the fluid pathway has a length greater than the length of the flexible bag. In some embodiments, the fluid pathway has a length at least about 20% longer than the length of the flexible bag. In some embodiments, the fluid pathway has a length of at least 10 cm. In some embodiments, the fluid pathway has a height or diameter from about 0.1 mm to about 4 mm. In some embodiments, the structure defining the fluid pathway comprises a plurality of openings to permit fluid to flow out of the fluid pathway as fluid passes through the apparatus. In some embodiments, the plurality of openings are about 10% to 90% of the surface area of the structure. In some embodiments, the plurality of openings are about 30% to 90% of the surface area of the structure. In some embodiments, the plurality of openings have a length of about 0.01 mm to about 20 mm. In some embodiments, the structure defining the fluid pathway is a tube connecting the first opening to the second opening. In some embodiments, the structure defining the fluid pathway is a transmission layer positioned within the interior of the flexible bag. In some embodiments, the transmission layer has a thickness between about 0.2 mm and about 3 mm. In some embodiments, the transmission layer comprises a woven mesh. In some embodiments, the transmission layer comprises high-density polyethylene. In some embodiments, the structure defining the fluid pathway is a channel within a section of the flexible bag. In some embodiments, the channel is welded into the section of the flexible bag. In some embodiments, the position of the fluid collection apparatus in use is orientation independent.

In some embodiments, the flexible bag bends from a released position to a bent position. In some embodiments, the flexible bag is in the released position, any portion of the flexible bag is aligned with its longitudinal axis; and when the flexible bag is in the bent position, a portion of the flexible bag is lifted away from the longitudinal axis to form an angle θ with respect to the longitudinal axis; and wherein the angle θ is measured from the released position to the bent position. In some embodiments, the portion of the flexible bag is lifted away from the longitudinal axis upon application of a force F applied individually to opposing ends of a first side of the flexible bag, and a reaction force R is applied to a midpoint of a second side of the flexible bag. In some embodiments, the angle θ is at least about 5°. In some embodiments, the angle θ is about 30° when the force F is between about 0.1N and about 20N. In some embodiments, the angle θ is about 30° when the force F is between about 1N and about 10N. In some embodiments, the flexible bag has a stiffness less than or equal to about 3 GPa. In some embodiments, the flexible bag has a fracture strain between about 10% and 500%. In some embodiments, the flexible bag comprises polyvinyl chloride, polypropylene, polyethylene, ethylene-vinyl acetate, or a combination thereof. In some embodiments, the flexible bag has a haze value between about 1% and about 30%. In some embodiments, the flexible bag has a thickness less than or equal to about 1 mm. In some embodiments, the flexible bag has a thickness less than or equal to about 0.5 mm.

In some embodiments, the interior of the flexible bag comprises a retained liquid, upon application of negative pressure to the interior of the bag via the outlet, the bag does not collapse to a height less than about 90% of the height of the bag prior to application of the negative pressure. In some embodiments, the negative pressure is between about 75 and about 125 mmHg below atmospheric pressure. In some embodiments, the flexible bag is expandable from a non-expanded state to a fully expanded state. In some embodiments, the height of the flexible bag in the non-expanded state is less than about 2 cm. In some embodiments, the weight of the fluid collection apparatus in the non-expanded state is less than about 150 g. In some embodiments, the volume of the flexible bag in the fully expanded state is at least about 20% greater than the volume of the flexible bag in the non-expanded state. In some embodiments, the height of the flexible bag in the fully expanded state is at least about 50% greater than the height of the flexible bag in the non-expanded state. In some embodiments, the flexible bag is configured to hold between about 50 mL and about 500 mL of fluid.

In some embodiments, the load-bearing component comprises an absorbent material. In some embodiments, the absorbent material absorbs at least about 50× its weight in water. In some embodiments, the absorbent material expands from a first thickness to a second thickness upon absorption of fluid, wherein the second thickness is less than or equal to the maximum thickness of the absorbent material. In some embodiments, the first thickness is between about 5 and 20 mm. In some embodiments, the maximum thickness is between about 20 and 100 mm. In some embodiments, the absorbent material retains at least about 80% of an absorbed fluid under a compression pressure applied to the flexible bag between about 10 and about 50 mmHg. In some embodiments, the fluid collection apparatus retains at least about 200 mL of an absorbed fluid under application of a compression pressure to the flexible bag between about 10 and about 50 mmHg. In some embodiments, the absorbent material comprises a polyacrylate, non-woven material, cellulose fibres, tissue paper, polyacrylamide copolymer, or a combination thereof. In some embodiments, the non-woven material comprises a polyester staple fibre. In some embodiments, the absorbent material is in a powder form, granular form, laminate form, or a combination thereof. In some embodiments, the load-bearing component comprises one or more pillars that resist compression of the flexible bag under a compression pressure of about 10 to about 50 mmHg, wherein the flexible bag does not compress to a height smaller than 90% of the height of the flexible bag prior to application of the compression pressure.

In some embodiments, the fluid collection apparatus further comprises a wicking material. In some embodiments, the wicking material is positioned adjacent to the load-bearing component within the interior of the flexible bag. In some embodiments, the wicking material absorbs fluid quickly and then distributes the fluid among the load-bearing component. In some embodiments, the wicking material comprises cellulose pulp, cotton, non-woven polyester, or a combination thereof. In some embodiments, a 0.05-2 mm layer of wicking material is positioned adjacent to the load-bearing component.

In some embodiments, the fluid collection apparatus further comprises an air passageway defined by a hydrophobic structure within the interior of the flexible bag. In some embodiments, the hydrophobic structure comprises gauze, reticulated polyurethane foam, or a combination thereof. In some embodiments, a layer of the hydrophobic structure is situated within the interior of the flexible bag, and the layer comprises a channel having a diameter between about 1 and about 10 mm defining the air passageway.

In some embodiments, the fluid collection apparatus further comprises a layer of transmissive material enclosing the load-bearing component within the interior of the flexible bag. In some embodiments, the transmissive material retains the load-bearing component while permitting fluid to pass through the transmissive material. In some embodiments, a 0.02-0.2 mm layer of the transmissive material encloses the load-bearing component. In some embodiments, the transmissive material comprises a non-woven spunbond polypropylene, cellulose fibres, non-woven HDPE or a combination thereof.

In some embodiments, the fluid collection apparatus further comprises a filter. In some embodiments, the filter comprises polytetrafluoroethylene.

In some embodiments, the fluid collection apparatus further comprises a body having an inlet and an outlet, wherein the first opening is contiguous with the inlet and the second opening is contiguous with the outlet. In some embodiments, the inlet and outlet are positioned within a single attachment point in the body. In some embodiments, the attachment point is configured to be in fluid communication with: a source of negative pressure at the outlet, and a wound dressing at the inlet. In some embodiments, the body covers an exterior side of the flexible bag. In some embodiments, the body comprises one or more viewing windows or openings. In some embodiments, the body comprises a material with a stiffness between about 0.1 GPa and about 10 GPa. In some embodiments, the inlet and the outlet are located within a port of the body, the port positioned over the first opening and the second opening of the flexible bag. In some embodiments, the inlet has a diameter of at least about 1 mm and the outlet has a diameter of at least about 1 mm.

In some embodiments, the fluid collection apparatus further comprises a panel covering a second exterior side of the flexible bag. In some embodiments, the panel comprises a fabric material.

In another aspect, provided herein is an orientation-independent fluid collection apparatus for negative pressure wound therapy comprising a flexible bag having a first opening and a second opening; wherein the bag comprises (a) a channel within a section of the flexible bag connecting the first opening and the second opening; and (b) a load-bearing component, wherein the fluid-collection apparatus in use is placed in an orientation independent manner. In some embodiments, the channel is welded into the section of the flexible bag. In some embodiments, the weld defines an interior of the bag that directs passage of fluid from the first opening to the second opening. In some embodiments, fluid flows in a circular direction.

Further provided herein is a system for collecting fluid from a wound, the system comprising the fluid collection apparatus and a wound dressing.

Further provided herein is a system for collecting fluid from a wound, the system comprising the fluid collection apparatus and a source of negative pressure.

Further provided herein is a system for collecting fluid from a wound, the system comprising the fluid collection apparatus and a connector, the connector configured to: connect the outlet of the apparatus to a source of negative pressure, and connect the inlet of the apparatus to the wound dressing.

In another aspect, provided herein is a method for collecting fluid from a wound site of a patient, the method comprising: (a) providing: (i) a fluid collection apparatus comprising an expandable bag having first opening and a second opening, an interior of the expandable bag comprising an absorbent material, and a pathway connecting the first opening and the second opening; wherein the pathway has a plurality of openings; (ii) a wound dressing positioned over the wound site, the wound dressing in fluid communication with the first opening of the fluid collection apparatus; and (iii) a source of negative pressure, the source of negative pressures in fluid communication with the second opening of the fluid collection apparatus; (b) applying a negative pressure from the source of negative pressure to the wound site via the fluid collection apparatus to draw fluid from the wound dressing, through the first opening of the expandable bag, and along the pathway; wherein the fluid is drawn through the plurality of openings of the pathway to the absorbent material as the fluid is drawn along the pathway; and (c) absorbing the fluid in the absorbent material; wherein the expandable bag expands during absorption. In some embodiments, the pathway has a length greater than the length of the expandable bag. In some embodiments, the pathway has a length at least about 20% longer than the length of the expandable bag. In some embodiments, the pathway has a length of at least about 10 cm. In some embodiments, the pathway has a height or diameter from about 0.1 mm to about 4 mm. In some embodiments, the plurality of openings have a length of about 0.01 mm to about 20 mm. In some embodiments, the pathway is defined by a structure connected to the first opening and the second opening. In some embodiments, the structure is a tube. In some embodiments, the structure is a transmission layer positioned within the interior of the expandable bag. In some embodiments, the transmission layer has a thickness between about 0.2 mm and about 3 mm. In some embodiments, the transmission layer comprises a woven mesh. In some embodiments, the transmission layer comprises high-density polyethylene. In some embodiments, the structure is a channel within a section of the expandable bag. In some embodiments, the channel is welded into the section of the expandable bag. In some embodiments, the expandable bag bends from a released position to a bent position. In some embodiments, the expandable bag is in the released position, any portion of the expandable bag is aligned with its longitudinal axis; and when the expandable bag is in the bent position, a portion of the expandable bag is lifted away from the longitudinal axis to form an angle θ with respect to the longitudinal axis; and wherein the angle θ is measured from the released position to the bent position. In some embodiments, the portion of the expandable bag is lifted away from the longitudinal axis upon application of a force F applied individually to opposing ends of a first side of the expandable bag, and a reaction force R is applied to a midpoint of a second side of the expandable bag. In some embodiments, the angle θ is at least about 5°. In some embodiments, the angle θ is about 30° when the force F is between about 0.1N and about 20N. In some embodiments, the angle θ is about 30° when the force F is between about 1N and about 10N. In some embodiments, the fluid collection apparatus is positioned next to the patient in an orientation-independent manner.

In some embodiments, the expandable bag has a stiffness less than or equal to about 3 GPa. In some embodiments, the expandable bag comprises polyvinyl chloride, polypropylene, polyethylene, ethylene-vinyl acetate, or a combination thereof. In some embodiments, the expandable bag has a haze value between about 1% and about 30%. In some embodiments, the expandable bag has a thickness less than or equal to about 1 mm. In some embodiments, the expandable bag has a thickness less than or equal to about 0.5 mm. In some embodiments, wherein upon application of the negative pressure, the expandable bag does not collapse to a height less than about 10% of the height of the expandable bag prior to application of the negative pressure. In some embodiments, the negative pressure is between about 75 and about 125 mmHg below atmospheric pressure. In some embodiments, the height of the expandable bag prior to absorption of fluid is less than about 2 cm. In some embodiments, the weight of the fluid collection apparatus prior to absorption of fluid is less than about 150 g. In some embodiments, the expandable bag expands from a first state to a second state during absorption of fluid; and wherein the second state is less than or equal to a fully expanded state. In some embodiments, the volume of the expandable bag in the fully expanded state is at least about 20% greater than the volume of the expandable bag in the first state. In some embodiments, the first state is a non-expanded state. In some embodiments, the height of the expandable bag in the fully expanded state is at least about 50% greater than the height of the expandable bag in the first state. In some embodiments, the expandable bag is configured to hold between about 50 mL and about 500 mL of fluid.

In some embodiments, the absorbent material absorbs at least about 50× its weight in water. In some embodiments, the absorbent material expands from a first thickness to a second thickness upon the absorption of fluid, wherein the second thickness is less than or equal to a maximum thickness of the absorbent material. In some embodiments, the first thickness is between about 5 mm and 20 mm. In some embodiments, the maximum thickness is between about 20 mm and 100 mm. In some embodiments, the absorbent material retains at least about 80% of the absorbed fluid under a compression pressure applied to the expandable bag between about 10 and about 50 mmHg. In some embodiments, the fluid collection apparatus retains at least about 80% of the absorbed fluid under a compression pressure applied to the expandable bag between about 10 and about 50 mmHg. In some embodiments, the absorbent material comprises a polyacrylate, non-woven material, cellulose fibres, tissue paper, polyacrylamide copolymer, or a combination thereof. In some embodiments, the non-woven material comprises a polyester staple fibre. In some embodiments, the absorbent material is in a powder or granular form.

In some embodiments, the interior of the expandable bag further comprises one or more pillars that resist compression of the expandable bag under a compression pressure of about 10 to about 50 mmHg, wherein the expandable bag does not compress to a height smaller than 90% of the height of the expandable bag prior to application of the compression pressure. In some embodiments, the expandable bag further comprises a wicking material. In some embodiments, the wicking material is positioned adjacent to the absorbent material within the interior of the expandable bag. In some embodiments, the wicking material absorbs fluid quickly and then distributes the fluid among the absorbent material. In some embodiments, the wicking material comprises cellulose pulp, cotton, non-woven polyester, or a combination thereof. In some embodiments, a 0.2-2 mm layer of wicking material is positioned adjacent to the absorbent material. In some embodiments, the expandable bag further comprises an air passageway defined by a hydrophobic structure. In some embodiments, the hydrophobic structure comprises gauze, reticulated polyurethane foam, or a combination thereof. In some embodiments, a layer of the hydrophobic structure is situated within the interior of the expandable bag, and the layer comprises a channel having a diameter between about 1 and about 10 mm defining the air passageway. In some embodiments, a layer of transmissive material encloses the absorbent material within the expandable bag. In some embodiments, the transmissive material retains the absorbent material while permitting the fluid to pass through the transmissive material. In some embodiments, a 0.02-0.2 mm layer of the transmissive material encloses the absorbent material. In some embodiments, the transmissive material comprises a non-woven spunbond polypropylene or a polyethylene mesh. In some embodiments, the fluid collection apparatus further comprises a filter. In some embodiments, the filter comprises polytetrafluoroethylene. In some embodiments, the fluid collection apparatus further comprises a body having a port, the port comprising an inlet contiguous to the first opening of the expandable bag, and an outlet contiguous to the second opening of the expandable bag. In some embodiments, the body covers a side of the expandable bag to block visibility of at least a portion of the expandable bag from the patient. In some embodiments, the body comprises one or more openings and the method further comprises the patient or a clinician viewing the fluid collected within the interior of the expandable bag through the one or more openings. In some embodiments, the body comprises a material with a stiffness between about 0.1 GPa and about 10 GPa. the fluid collection apparatus further comprises a panel covering a side of the expandable bag; and wherein when the fluid collection apparatus is situated next to the patient, the panel is positioned between the expandable bag and the patient. In some embodiments, the panel comprises a fabric material.

DETAILED DESCRIPTION OF THE INVENTION

Figure 1:
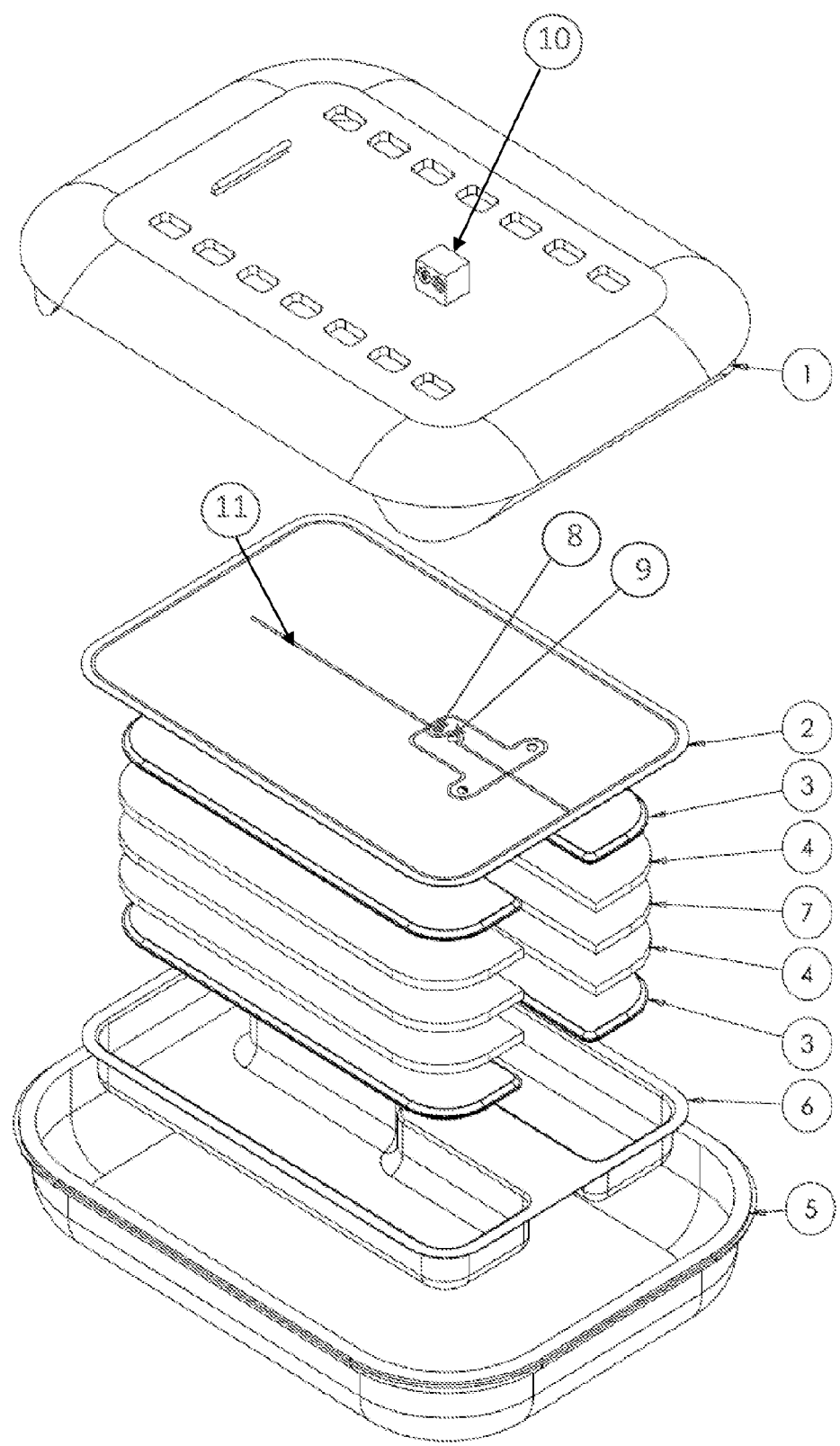
FIG. 1 shows an exploded view of an exemplary fluid collection apparatus.

Medical procedures often involve the removal of fluid from a patient, including for example, during negative pressure wound therapy. For negative pressure therapies, a source of negative pressure such as a suction pump is used to apply negative pressure to a site on or in the patient to draw fluid from the site. Fluid may be collected in a dressing positioned over the site and/or in a canister. Typical canisters used in negative pressure systems are rigid in order to withstand and maintain the application of negative pressure. However, this rigidity results in a canister with bulk that is often costly, takes up significant storage space, adds weight and is not discrete in use. A canister which is flexible and expandable during use would mitigate these problems by having a small footprint while providing the benefit of being soft to the touch and comfortable for the patient.

In one aspect, provided are bags or flexible reservoir for collecting fluid from a patient comprising a low stiffness material such that the bags are flexible and relatively small when empty, and capable of maintaining a negative pressure in a system. The bags comprise a first opening for receiving fluid and a second opening for attachment to a negative pressure source. For negative pressure wound therapies, the first opening is configured to be in fluid communication with a wound site such that upon application of negative pressure from the negative pressure source via the second opening, fluid is drawn from the wound site, through the first opening, and into the bag. The bag comprises a fluid pathway connecting the first and second openings to direct the passage of fluid through the bag. In many cases, the fluid pathway has a length longer than the length of the bag, and the fluid pathway directs fluid to multiple regions within the path of the fluid pathway by releasing fluid through perforations or openings within the fluid pathway. Fluid pathways are defined by, for example, a tube or channel that provide fluid connection between the first opening and the second opening of the bag. In some cases, a fluid pathway is defined by a weld of a flexible bag that creates a space for fluid to flow through a material bound within the space. Such materials include porous/open transmission materials, where fluid flows through a layer of this material to adjacent absorbing material. The distribution of fluid within the thickness of the absorbing material may not be defined by a structure, and can distributed without a defined pathway to communicate with surrounding absorbing material and maximize opportunity for fluid absorption.

The bag is able to withstand the application of negative pressure without completely collapsing by comprising a load-bearing component in the interior of the bag. In some embodiments, the load-bearing component is an absorbent material that absorbs fluid received in the bag. In some such cases, the fluid pathway distributes fluid to the absorbent material through passage of the fluid through a plurality of openings within the pathway. In some embodiments, the load-bearing component is a plurality of pillars that provide a physical structure that prevents the bag from collapsing below a threshold height upon application of negative pressure to the bag. In some embodiments, a bag comprising a load-bearing component such as an absorbent material or pillars, withstands applications of negative pressure up to about 125 mmHg without collapsing to a height less than about 90% of the height of the bag prior to application of negative pressure. In some cases, the load-bearing component is an absorbent material and in the absence of an absorbed fluid, the bag collapses upon application of negative pressure. However, in some such instances, as fluid is drawn into the bag by an applied negative pressure, and then absorbed and retained by the absorbent material, the absorbent material and retained fluid provide a support for the bag, and under continued negative pressure the bag resists collapse and release of retained fluid. In some cases where the bag comprises an absorbent material, the absorbent material is configured to expand upon absorption of fluid drawn into the bag during negative pressure application. If the bag is an expandable bag, as the absorbent material expands during absorption, the expandable bag may also expand.

In some embodiments, a bag provided herein is expandable from a first or a non-expanded state to a second expanded state upon retention of fluid. The volume of the bag in the second expanded state is less than or equal to the volume of the bag in the fully expanded state of the bag. As fluid is drawn into the bag and retained, the expandable bag expands to accommodate the increasing volume of fluid drawn into the bag. In exemplary embodiments, fluid drawn into the bag is retained by absorption into a superabsorbent polymer.

Figure 2:
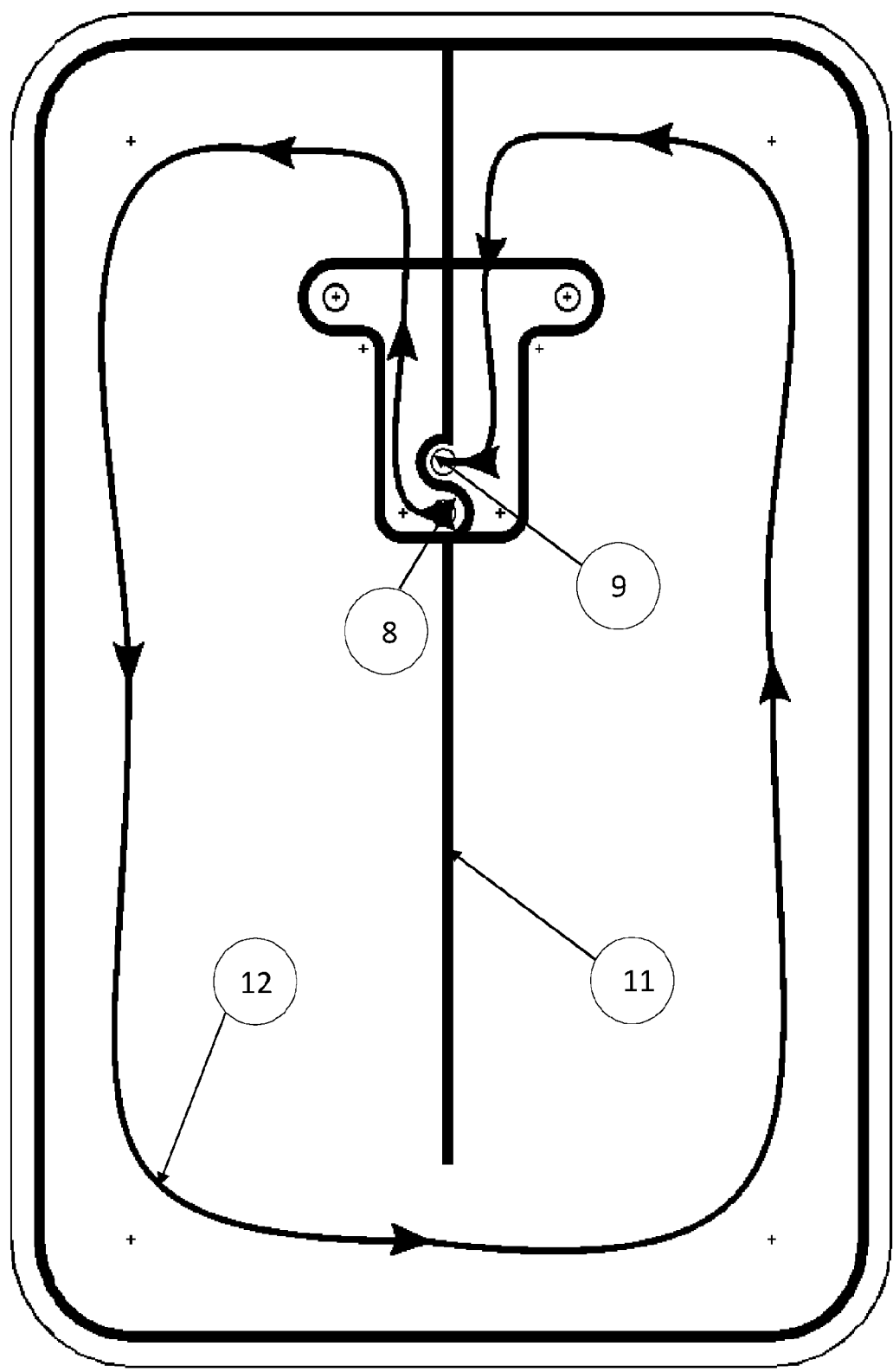
FIG. 2 shows an exemplary path for fluid flow within a bag of a fluid collection apparatus.

An exemplary apparatus for collecting fluid comprising a bag described herein is shown in an exploded view in FIG. 1. The bag is comprised of a top layer 2 welded to a bottom layer 6 of bag material. The top layer 2 comprises a first opening 8 and a second opening 9 positioned in close proximity to one another. A fluid pathway 12 within the interior of the bag (FIG. 2) connects the first and second openings to direct the passage of fluid through the interior of the bag. The fluid pathway 12 is defined in part by a weld 11. The fluid pathway 12 is defined by a structure comprising a plurality of perforations (not shown) that allow fluid drawn into the bag to be released from the pathway into other regions of the bag. As shown in FIG. 2, the weld 11 forces fluid drawn into the bag through a first opening 8 to follow a circulative path 12 towards a second opening 9, through which negative pressure is applied to draw the fluid in. The bag comprises a transmission layer 7, which provides a structure for the fluid pathway. Adjacent to the transmission layer on both sides are layers of wicking material 4. Opposite the transmission layer side of the wicking material is a layer of absorbent material 3. As fluid is drawn through the fluid pathway 12 of the bag, the fluid is released to the wicking layer 4 and then distributed to the absorbent material 3, where the fluid is absorbed. The exterior of one side of the bag comprises a body 1 having a port 10. Port 10 comprises an inlet that aligns with the first opening of the bag and an outlet that aligns with the second opening of the bag. Another side of the bag comprises a fabric panel 5 that connects with the body 1 to enclose the bag. An exemplary fluid pathway for an apparatus such as the one depicted in FIG. 1 is shown in FIG. 2, as further detailed elsewhere herein.

Another exemplary apparatus for collecting fluid is shown by different views in FIGS. 3-7. The bag of the apparatus is comprised of a top layer 305 welded to a bottom layer 301.

Figure 3:
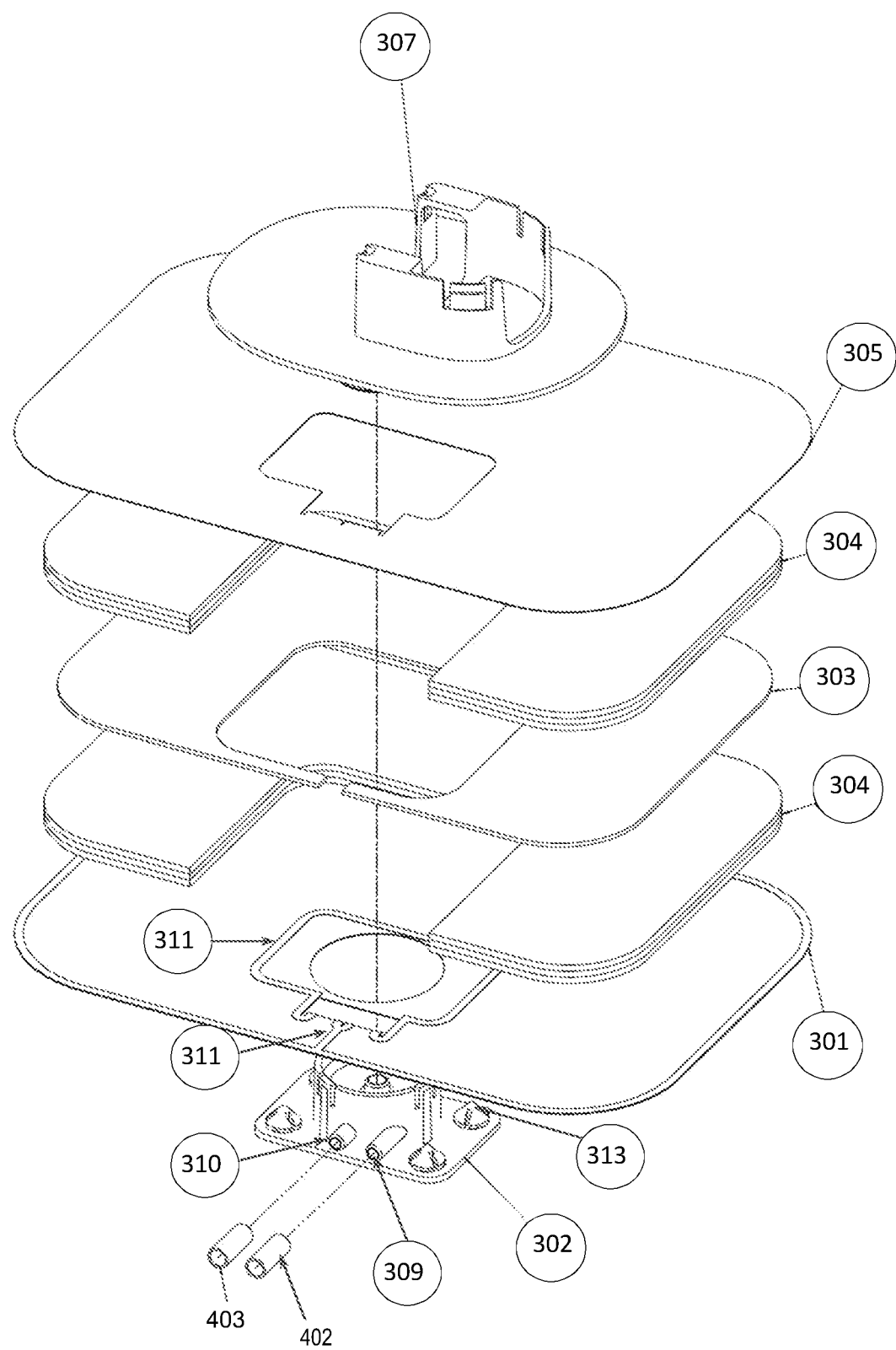
FIG. 3 shows an exploded view of an exemplary fluid collection apparatus.
Figure 4:
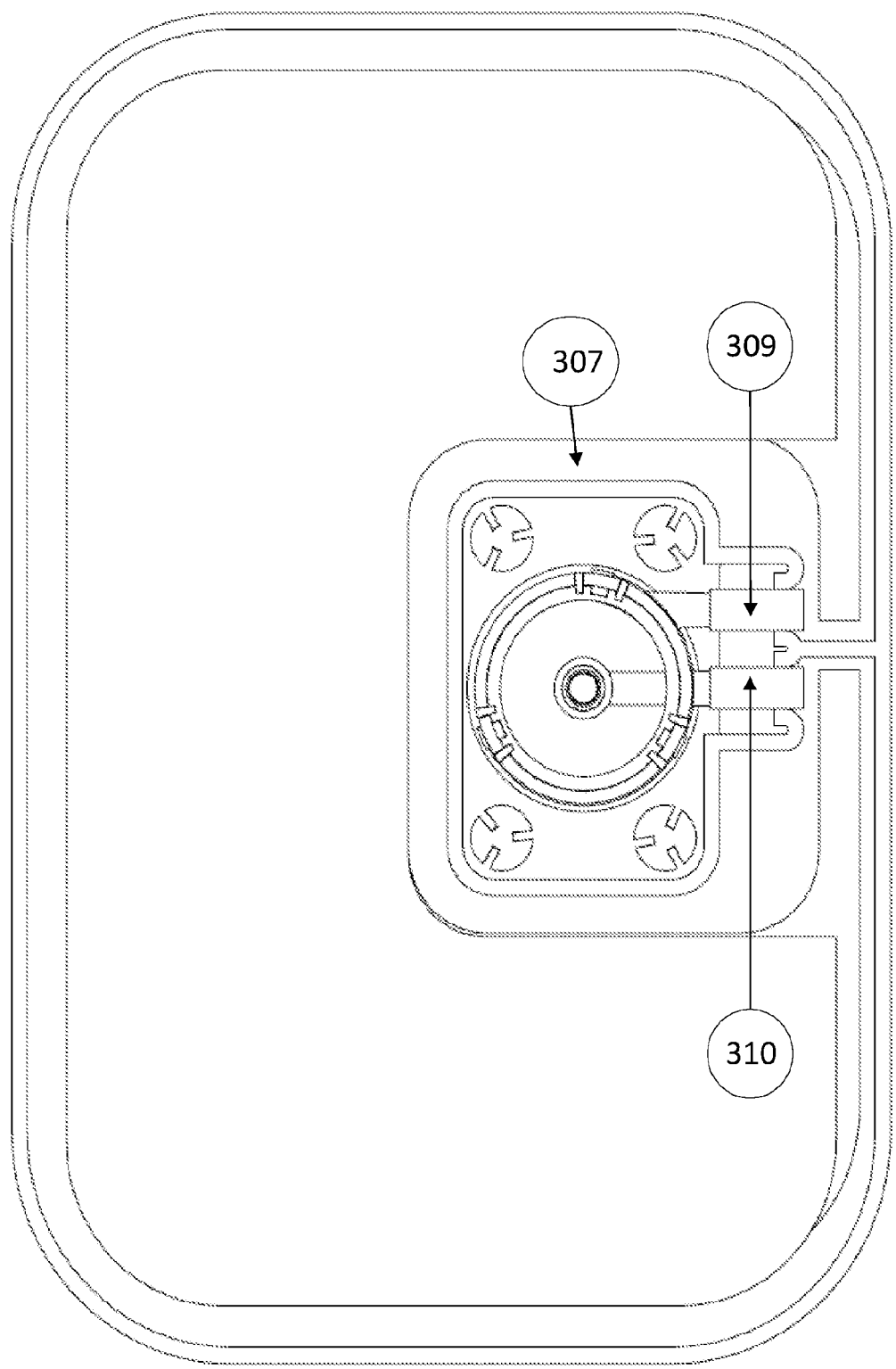
FIG. 4 shows a birds-eye view of the fluid collection apparatus of FIG. 3
Figure 5A:
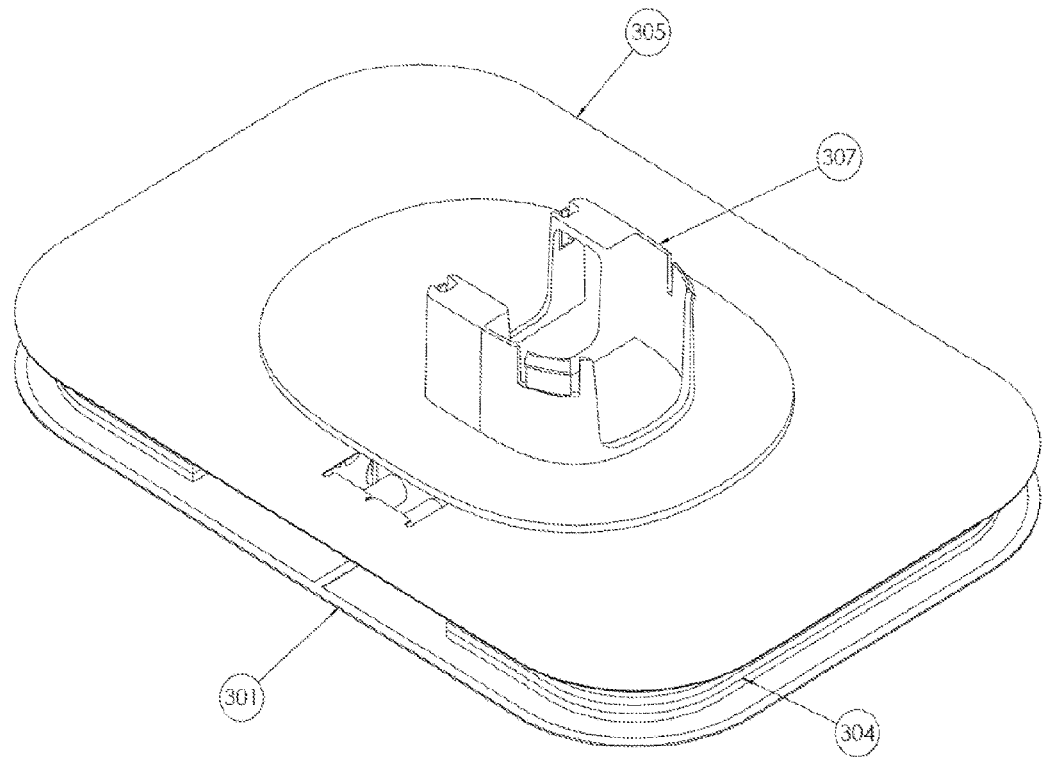
FIG. 5A shows a top-side view of the fluid collection apparatus of FIG. 3.
Figure 5B:
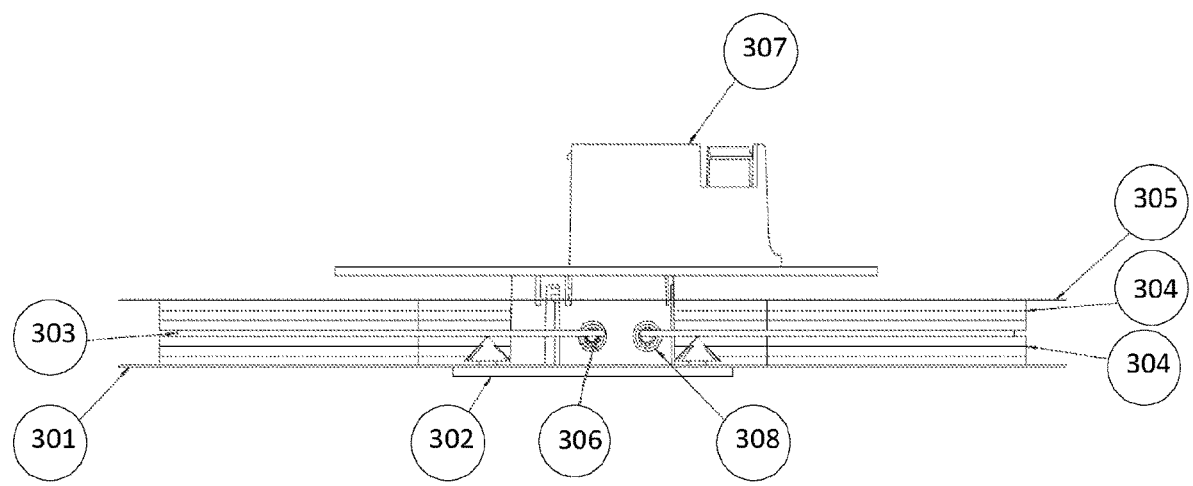
FIG. 5B shows a side view of the fluid collection apparatus of FIG. 3.
Figure 6:
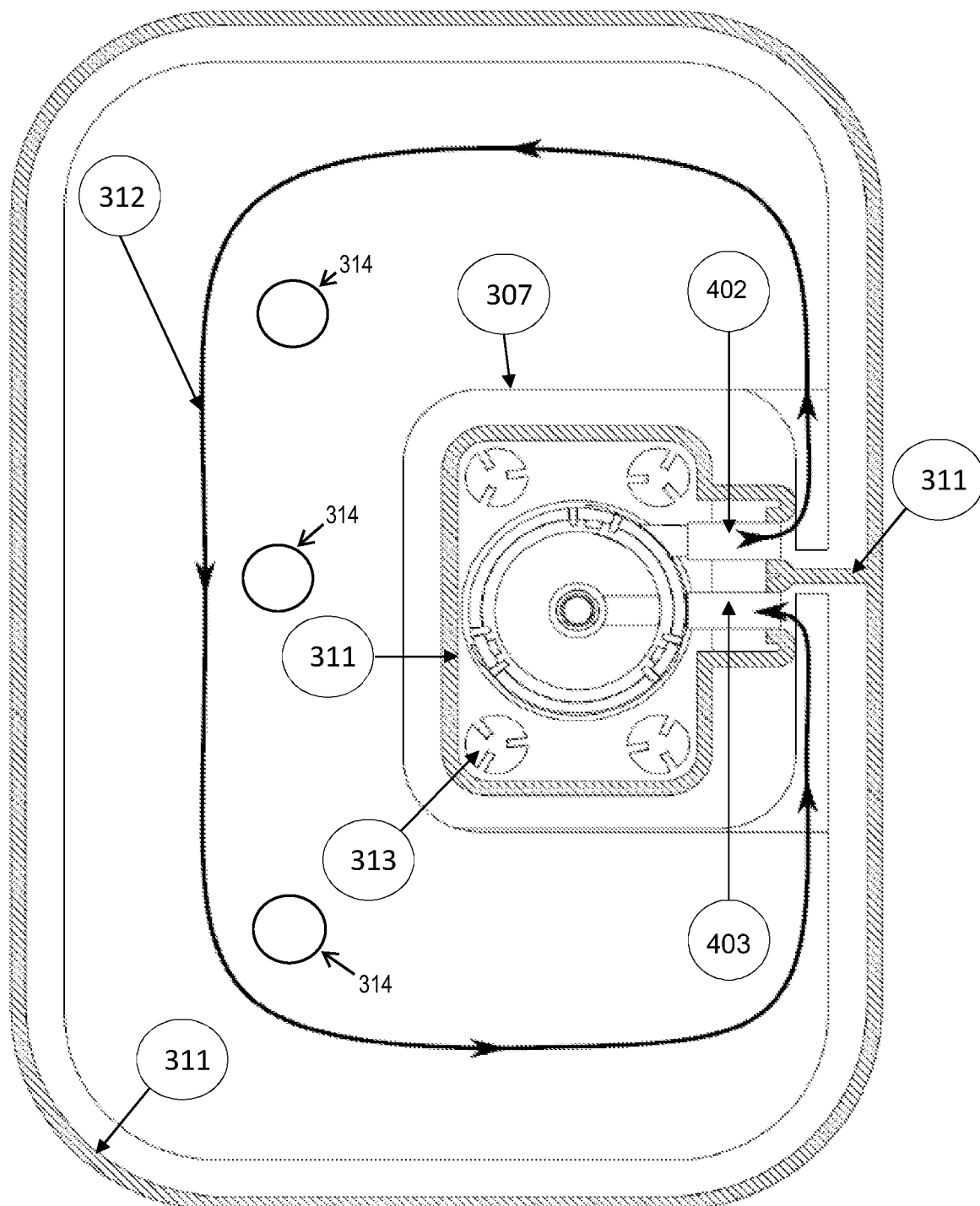
FIG. 6 shows a birds-eye view of an exemplary fluid pathway in the fluid collection apparatus of FIG. 3.
Figure 7:
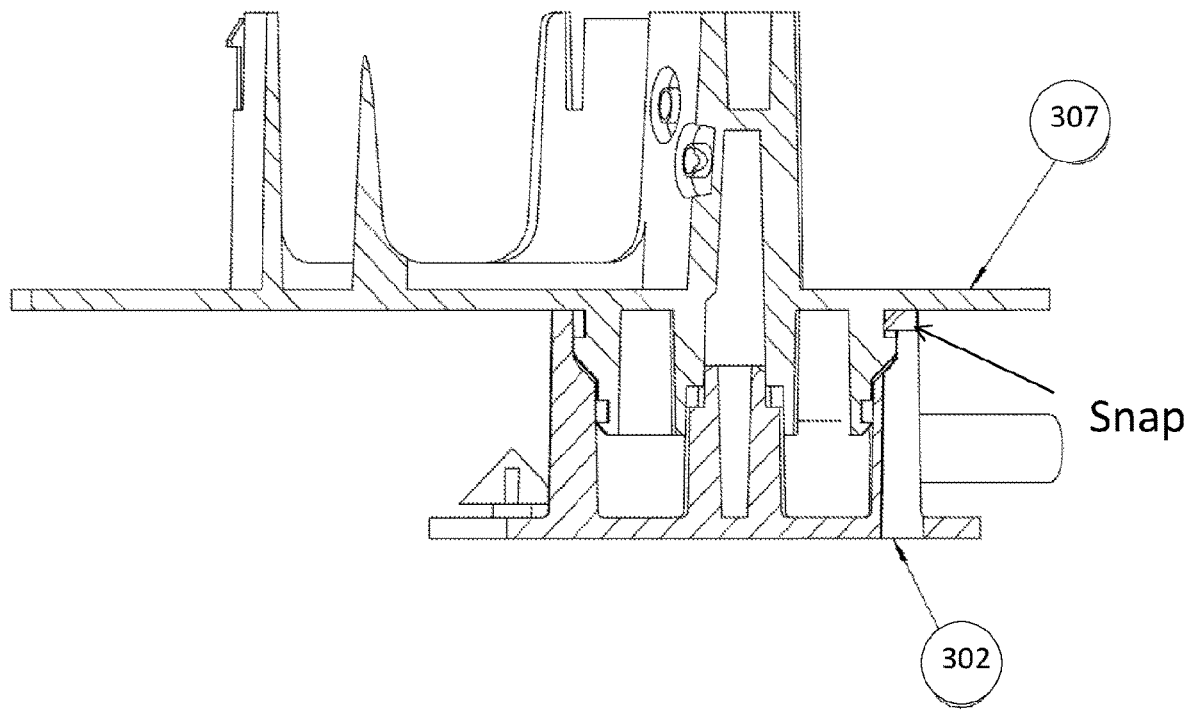
FIG. 7 shows a side view of the moulded parts in the fluid collection apparatus of FIG. 3, with upper and lower mouldings snap fitted together.

The weld defines an interior of the bag that directs passage of fluid from inlet 402 towards outlet 403, where liquid is absorbed during the passage such that only air escapes through outlet 403. An exemplary fluid pathway 312 is shown in FIG. 6. There is a weld 311 between inlet 402 and outlet 403 that forces fluid to flow in a circular direction. An advantage of this circular path is that it contributes to orientation independence of the bag in use. The circular path means that as air and liquid (e.g., exudate) is drawn through the canister, the liquid has a longer distance to travel, which takes a longer period of time. This allows additional time for the liquid to be absorbed by the transmission layer and distributed to the super absorbing polymer. By preventing the air and liquid flow from flowing directly from the inlet to the canister, to the outlet of the canister, the fluid is absorbed and prevented from reaching the outlet irrespective of the orientation of the canister. Within the bag is transmission layer 303, which transmits the fluid along the fluid pathway. Openings within transmission layer 303 (openings not shown) permit liquid to be absorbed by adjacent super absorbent polymer layers 304. As shown in FIG. 3, there is a hole within the middle of layers 305, 304, 303, and 301, through which two mouldings, upper moulding 307 and lower moulding 302 snap together, trapping the bag and allowing it to interface with the fluid flow from and to the rest of the device. As shown in FIG. 6, a plurality of pillars 314 provide a physical structure that prevents the bag from collapsing below a threshold height upon application of negative pressure to the bag. A close side view of the snap connection is shown in FIG. 7. The lower moulding 302 comprises an inlet 309 and an outlet 310, each with a respective tube 306, 308 mounted thereon. The inlet tube 308 is configured to connect to a wound dressing while the outlet tube 306 connects to the pump. The tubes 306, 308 are sandwiched between the outer layers of the bag (305, 301) and form the inlet 402 and the outlet 403 of the bag. The lower moulding 302 shows a series of four barbs 313, which in an embodiment can be used to push the bag onto. However, in many embodiments, the bag is tack welded to the lower moulding 302 and thus the barbs 313 may not be necessary.

The apparatus and features thereof shown in FIGS. 1-7 are for illustrative purposes only and it is intended that a fluid collection apparatus may comprise additional components and/or lack one or more components shown. For example, one or more layers of wicking material, transmission layer, and/or cover may not be necessary for the fluid collection apparatus to function as described. As a further example, the fluid collection apparatus may not comprise multiple layers of a material, such as an absorbent material and/or wicking layer as illustrated in FIG. 1.

As used herein, a fluid is inclusive of a liquid and/or gas. As a non-limiting example, fluid drawn into the bag during a negative pressure therapy comprises a mixture of liquid and gas, and the liquid is retained within the bag. In some cases, a fluid comprising a mixture of liquid and gas is retained within the bag. In some cases, the bag comprises an absorbent material configured to absorb and retain liquid from a fluid drawn into the bag, where the fluid drawn into the bag comprises the liquid or a mixture of the liquid and a gas. In further cases, at least some of a gas drawn into the bag is retained within the bag. In other cases, there is no net increase of gas in the bag during a negative pressure therapy, and instead, there may be a net decrease of gas in the bag during negative pressure therapy.

Fluid Collection Bag

Bags for collecting fluid described herein are comprised of a low stiffness material such that the bags are flexible and comfortable for use in negative pressure therapies. For example, a bag for collecting fluid, or a material thereof, has a stiffness less than or equal to about 3 GPa, 2 GPa, 1 GPa, 0.5 GPa, 0.4 GPa, 0.3 GPa or 0.2 GPa. In some cases, the stiffness is between about 1 MPa and about 3 GPa, or between about 1.5 MPa and about 1 GPa. The stiffness may be measured by any technique known in the art, including, without limitation, a force-displacement test, $E=(f1)/(xa)$, where f is the applied force, 1 is the unloaded bag length, x is the change in bag length and a is the area of the bag. Commercially available force displacement equipment is supplied by a number of manufactures such as the MultiTest 5-Xt supplied by Mecmesin Ltd. Newton House, Spring Copse Business Park, Slinfold, West Sussex, UK and the M350-5 AT supplied by The Testometric Company Ltd, Unit 1, Lincoln Business Park, Lincoln Close, Rochdale UK. These machines are capable of applying strain to a clamped material sample at a defined rate through controlled movement along a linear slide. While the strain is applied the instruments measure and data log the applied load and displacement by using a strain gauge force sensor and linear encoder. The combination of load and displacement can then be used to characterize the material. In some embodiments, a bag for collecting fluid has a flexibility measurable by applying a force F perpendicularly to the longitudinal axis at two opposing ends of a first side of the bag, applying a reaction R to the center of an opposing side of the bag, and measuring an angle $\theta$ at which the bag bends, where R is equal to $2F*\cos(o)$. As a non-limiting example, the bag bends from a released position to a bent position, where any portion of the bag is aligned with its longitudinal axis when the bag is in the released position, and the bag is in the bent position when the forces F and R are applied to lift a portion of the bag away from the longitudinal axis and form an angle $\theta$ with respect to the longitudinal axis. The angle $\theta$ is measured from the released position to the bent position. In some embodiments, a flexible bag has a $\theta$ of at least about 5, 6, 7, 8, 9, 10, 15, 20, 25, 30, 35 or 40° when the flexible bag is empty and/or comprises one or more absorbing materials prior to collection of fluid. In some cases, the F is about 0.1-20N, 1-10N, or 1-5N.

In some embodiments, a bag for collecting fluid is capable of non-elastic strain or plastic deformation, wherein upon removal of applied forces F and R, the angle $\theta$ does not decrease to zero. As a non-limiting example, a flexible bag described herein bends to a first deformation angle $\theta 1$ upon application of forces F and R, and upon removal of the forces F and R, the deformation angle is maintained at about $\theta 1$ or is decreased to about $\theta 2$. In some cases, $\theta 2$ is at least about 50%, 60%, 70%, 80%, or 90% of $\theta 1$. As described herein, plastic deformation is measurable when the bag is: empty, comprises one or more absorbing materials, and/or comprises one or more absorbing materials retaining an absorbed liquid. In some embodiments, a flexible bag has a $\theta 1$ of at least about 5, 6, 7, 8, 9, 10, 15, 20, 25, 30, 35 or 40° when the flexible bag is empty and/or comprises one or more absorbing materials prior to collection of fluid. In some cases, when F is about 1-5N and R is about 1-10N, $\theta 1$ is about 15-45° and $\theta 2$ is about 1-10°. In some cases, when F is about 3.2N and R is about 5.5N, $\theta 1$ is about 30° and $\theta 2$ is about 5°.

In some embodiments, a bag for collecting fluid has a strength or toughness such that the bag withstands forces applied to the bag during use without rupturing. In some cases, the bag of a material thereof has a fracture strain between about 5% and 500%. In some cases, the bag or a material thereof has a fracture strain between about 10% and about 100%. Similar equipment used for measuring force displacement may be utilized, such as commercially available force displacement equipment supplied by manufactures such as the MultiTest 5-Xt supplied by Mecmesin Ltd. Newton House, Spring Copse Business Park, Slinfold, West Sussex, UK and the M350-5 AT supplied by The Testometric Company Ltd, Unit 1, Lincoln Business Park, Lincoln Close, Rochdale UK. A sample can be clamped and be extended in tension by the machine at a defined rate. By measuring the load and displacement the strain at fracture can be established by inspection of the logged stress data. A sudden reduction to zero seen by the load cell is a clear indication of when fracture occurred.

A bag for collecting fluid may be comprised of a single unit of one or more materials, or as two or more pieces or layers welded together or otherwise connected. In some cases, a bag is comprised of multiple layers of materials that serve as a liquid barrier. Exemplary materials for constructing a bag for fluid collection include polyvinyl chloride (PVC), polypropylene, polyethylene, ethylene-vinyl acetate, or a combination thereof. In some cases, the bag comprises PVC. In some cases, the bag comprises multiple layers of laminate material, such as a combination of low-density polyethylene (LDPE) and ethylene-vinyl acetate (EVA), e.g., LDPE-EVA-LDPE. In some embodiments, a bag material is selected that maintains a flexibility and/or low stiffness at a given thickness, as well as provides a barrier to prevent escape of liquid from an interior of the bag through the bag material. For some cases wherein the interior of the bag comprises an absorbent material or structure for retaining liquid within the bag, the bag does not necessarily require a material that serves as a liquid barrier. Accordingly, in some cases, a bag comprised of any flexible plastic film is envisioned for use in fluid collection as described herein. As a non-limiting example, a bag comprises a single layer of material such as polypropylene, low-density polyethylene, or polyurethane. In some embodiments, a fluid collection bag, having a single or multiple layered bag material, has a thickness less than or equal to about 1 mm, 0.5 mm, 0.4 mm, 0.3 mm, 0.2 mm, 0.1 mm, or 0.05 mm. In some cases, a fluid collection bag material has a thickness between about 0.01 mm and 0.2 mm, or about 0.01 mm and 0.5 mm. For a fluid collection apparatus having a bag comprising an absorbent material enclosed within the bag, exemplary heights of the bag with the absorbent material include from about 5 mm to about 20 mm, or about 10 mm to about 15 mm. In various embodiments, a height of a fluid collection apparatus comprising a flexible bag and an enclosed absorbent material is less than about 20 mm. In some embodiments, the bag comprises a transparent material configured to allow viewing of the interior of the bag from the exterior of the bag. As a non-limiting example, the transparent material allows for a patient or clinician to view a characteristic and/or level of exudate retained within the bag during negative pressure wound therapy. In other embodiments, the bag comprises a material that obscures a clear view of the interior of the bag such that a level of retained fluid within the bag and liquid color is still detectable from viewing the exterior of the bag, however, detailed aspects of the retained fluid are not readily apparent. For example, the bag may comprise a layer of a privacy film or frosting. In some cases, the bag has a haze value of at least about 1%, or between about 1% and about 30%. As understood by one skilled in the art, haze may be measured using haze meters and spectrophotometers. The Haze level may be determined under ASTM standards.

In some embodiments, a bag for collecting fluid is expandable such that the bag expands from a first state to a second state as fluid is drawn into the bag. In some cases, the first state is a non-expanded state and the second state is less than or equal to a fully expanded state. A non-expanded state includes both: a state in which the bag is not connected to negative pressure and may comprise air from the environment, and a state in which the bag is connected to a negative pressure source and air is drawn out of the bag under the negative pressure. For the latter case, when the bag comprises an absorbent material as a load-bearing component, in the absence of liquid in the bag, a non-expanded state includes the state of the bag under negative pressure and before absorption and retention of liquid. As such, a fully expanded state of a bag comprising an absorbent material includes the state of the bag when the absorbent material has reached a capacity at which no additional liquid is absorbable and/or retainable within the absorbent material. Further, for cases where the bag comprises a plurality of pillars as a load-bearing component, in the absence of liquid in the bag, a non-expanded state includes the state of the bag under negative pressure, where air is present in gaps between two pillars, as well as between a pillar and an wall of the bag. In some embodiments, wherein the bag comprises an absorbent material, the height of the bag in the non-expanded state is less than about 20 cm, 15 cm, or 10 cm. In some embodiments, the height of a bag in a non-expanded state comprising an absorbent material is between about 5 mm and 20 mm, or between about 10 mm and about 15 mm. In some embodiments, the volume of the bag in the fully expanded state is at least about 20%, 30%, 40%, 60%, 70%, 80%, 90%, 100%, 150%, 200%, 250%, 300%, 350%, or 400% greater than the volume of the bag in the non-expanded state. In some cases, the volume of the bag in the fully expanded state is between about 100% and about 500%, or between about 200% and about 400% greater than the volume of the bag in the non-expanded state. As a non-limiting example, a bag comprising an absorbent material has an initial volume of about 100 mL and expands to a final volume of about 400 mL. For cases wherein a bag comprises a support pillar or non-absorbing structure, the internal volume of the bag expands upon retention of fluid by a smaller degree, such as less than about 20%, or does not expand at all. In some cases, the height of the bag in the fully expanded state is at least about 20%, 30%, 40%, 60%, 70%, 80%, 90%, 100%, 150%, 200%, 250%, 300%, 350%, or 400% greater than the height of the bag in the non-expanded state. For instances wherein the bag comprises two almost parallel sheets of material welded or otherwise bound together, the increase in height upon fluid retention correlates to a decrease in width to allow for internal volume expansion. In some embodiments, the interior of the bag is configured to hold about 50-500 mL, 50-400 mL, 50-300 mL, 50-200 mL, 100-500 mL, 100-400 mL, 100-300 mL, or 200-300 mL. In some embodiments, the weight of the bag in the non-expanded state, including materials within the bag, such as absorbent material, is between about 50 g and 150 g or between about 80 g and 120 g.

In an exemplary embodiment, a bag for collecting fluid is an expandable bag comprising an absorbent material, where the expandable bag has a stiffness between about 1.5 MPa and about 1 GPa. Such a bag is capable of plastic deformation and as such, can maintain a second deformation angle that is at least about 50% of a first deformation angle after the applied forces F and R to generate the first deformation angle are released. The expandable bag comprises a material such as polyvinyl chloride or polyolefin-EVA laminate film configured to expand in height to accommodate retained fluid. In some cases, the bag comprises an absorbent material, wherein the height of the bag and absorbent material is between about 10 and about 15 mm. In some embodiments, the bag comprises a tube or channel, for example, within a transmission layer, which defines a fluid pathway between a first opening and a second opening in the bag, wherein the tube or channel comprises a plurality of openings for distributing fluid drawn through the first opening to the absorbent material. In some cases, the tube or channel has a length that is at least about 50%, 60%, 70%, 80%, 90% or 100% longer than a length of the bag. In some cases, the tube or channel has a length that is about 50% to about 100%, or about 75% to about 100% longer than a length of the bag. For bags having circular or eclipsed shapes, a length is inclusive of a diameter.

Fluid Pathway

A bag for fluid collection provided herein comprises a fluid pathway connecting a first opening in the bag to a second opening in the bag. The fluid pathway is configured to distribute liquid entering through the first opening through the interior of the bag as the fluid is drawn through the bag. In many cases, the structure and welding of the bag defines the fluid pathway. In some such cases, a transmission layer comprising openings along the fluid pathway distributes liquid throughout the pathway. In some embodiments, the length of the fluid pathway is from about 10 cm to greater than about 10 m, or about 10-1000 cm, 10-900 cm, 10-800 cm, 10-700 cm, 10-600 cm, 10-500 cm, 10-400 cm, 10-300 cm, 10-200 cm, 10-100 cm, or 10-50 cm. In some cases, the length of the fluid pathway is greater than the length of the bag. As non-limiting examples, the length of the fluid pathway is about or at least about 10%, 20%, 30%, 40%, 50%, 60%, 70%, 80%, 90%, 100%, 150%, 200%, 250%, or 300% greater than the length of the bag. In various embodiments, the fluid pathway is a tube or channel within a transmission layer positioned inside the bag, wherein as fluid flows through the fluid pathway between the first opening and the second opening, it is wicked and/or absorbed to other materials within the bag. As a non-limiting example, liquid is wicked from the transmission layer to an absorbing material where the liquid is retained. In some embodiments, a transmission layer is any structure which allows transport of liquid and air while staying open under pressure.

In some embodiments, the fluid pathway is defined by a physical structure comprising a plurality of openings or perforations that release liquid from the structure into other regions of the bag configured to retain the liquid. For example, the other regions of the bag comprise an absorbent material configured to absorb and retain the liquid released from the fluid pathway. In exemplary implementations, the fluid pathway is configured to distribute liquid throughout the other regions so that bag is orientation-independent. In some cases, the physical structure connecting the first opening and the second opening in the bag is a tube comprising a plurality of openings. In some cases, the physical structure connecting the first opening and the second opening is a channel within a section of the bag, for example, a transmission layer residing within the bag. In some cases, the channel is welded into the section of the bag. In some embodiments, the fluid pathway has a height or diameter from about 0.1 mm to about 4 mm. In some cases, the openings make up from about 20% to about 50% of the total surface area of the physical structure, such as a channel or tube.

Non-limiting depictions of configurations of fluid pathways are shown in FIGS. 2 and 6. In each figure, the fluid pathway 12, 312 begins at a first opening 8, 309 and curves around the bag to the second opening 9, 310. In some embodiments, a tortuous pathway configuration like the one depicted in FIG. 2 enables fluid to flow in close proximity to absorbent material within the bag, and increases the residence time of the fluid next to the absorbent material. Because absorbency of some absorbent materials such as superabsorbent materials is diffusion driven, this proximity increases the total amount of fluid absorbed per unit weight of absorbent. For example, when a bag comprises a superabsorbent material, under application of negative pressures suitable for use in NPWT (e.g., 75 to 125 mmHg below atmospheric pressure), the superabsorbent material absorbs between about 4 g and 10 g of 0.9% NaCl solution per unit weight of the superabsorbent material. For cases wherein a bag comprises a pillar or non-absorbing load-bearing material, fluid absorbed per unit weight of the pillar or non-absorbing load-bearing material is from about 25:1 to about 75:1, or about 50:1.

In some embodiments, the bag comprises a filter located near the end of the fluid pathway and the second opening to retain liquid within the bag. In some cases, the filter is located adjacent the second opening, either on the interior or exterior, or within the opening. In some embodiments, the filter comprises a hydrophobic PTFE plug or membrane.

Load-Bearing Component

A bag for fluid collection provided herein comprises a load-bearing component that withstands application of negative pressure to the interior of the bag. In some cases, upon application of negative pressure to the interior of the bag via the second opening in the bag, the bag does not collapse to a height less than about 90% of the height of the bag prior to application of the negative pressure. In some cases, before liquid is drawn into the bag during a NPWT application, the bag collapses to a height less than about 90% of the height of the bag prior to the application of the negative pressure as air is drawn out of the bag. For instance, applications of negative pressure include between about 75 mmHg and about 125 mmHg below atmospheric pressure. For expandable bags, when fluid is drawn into the expandable bag during use in a fluid collection therapy with negative pressure, the bag expands in height as it retains fluid. In some embodiments, the load-bearing component comprises one or more absorbent materials. As a non-limiting example, the load-bearing component comprises two or more materials. In some cases, the absorbent material expands upon absorption of fluid. If the bag is an expandable bag, the expansion of the absorbent material may coincide with the expansion of the expandable bag. In some cases, the load-bearing component comprises one or more pillars that resist compression of the bag to less than a threshold height. In some cases, the load-bearing component comprises both an absorbent material and one or more pillars.

In some aspects, an absorbent material within a bag described herein comprises a super absorbent material. Non-limiting examples of super absorbent materials include a material or combination of materials that absorb about or at least about 10-, 20-, 30-, 40-, 50-, 60-, 70-, 80-, 90-, 100-, 120-, 140-, 160-, 180-, 200-, 250-, 300-, 400-, or 500-times the super absorbent material's weight in water. In some cases, a super absorbent material absorbs about 20-500 times its weight in water, or absorbs about 50-500 times its weight in water. When the super absorbent is used in a bag for retaining biological fluids having salinity such as exudates, the super absorbent fluid may absorb between about 4 and about 10 times its weight in a saline liquid.

In some aspects, an absorbent material within a bag described herein expands from a first thickness to a second thickness upon absorption of fluid, wherein the second thickness is less than or equal to the maximum thickness of the absorbent material. In some embodiments, the first thickness refers to the thickness of the absorbent material prior to absorption of fluid during a negative pressure therapy. For example, the first thickness is the thickness of the expandable absorbent material supplied and/or stored with a fluid collection bag and/or apparatus for use in negative pressure therapy. In some embodiments, the absorbent material is a super absorbent material that expands during absorption of fluid. In some cases, the first thickness of the expandable absorbent material is between about 3 mm and 15 mm, or between about 5 mm and 10 mm. In some cases, the maximum thickness is between about 15 mm and 50 mm, or between about 20 mm and 35 mm. In some cases, the maximum thickness of the expandable absorbent material is about 1.2-, 1.4-, 1.6-, 1.8-, 2-, 2.5-, 3-, 3.5-, 4-, 4.5- or 5-times the first thickness. In some cases, the maximum thickness of the expandable absorbent material is about 1.5-5, 1.5-4, 1.5-3, 1.5-2.5, or 1.5-2 times the first thickness.

In some embodiments, the absorbent material retains at least about 80% of an absorbed fluid under an additional compression pressure applied to the bag between about 10 and about 50 mmHg. In some embodiments, the bag comprising the absorbent material retains at least about 80% of an absorbed fluid under a compression pressure applied to the bag between about 10 and about 100 mmHg. In some embodiments, the absorbent material retains at least about 200 mL of an absorbed fluid under application of a compression pressure to the bag between about 10 and about 100 mmHg. In some cases, the absorbent material retaining the fluid comprises a superabsorbent material.

Non-limiting examples of absorbent materials provided within a bag for collecting fluid described herein include compositions comprising a polyacrylate, non-woven material, cellulose fibres, tissue paper, polyacrylamide copolymer or a combination thereof. A non-woven material includes a polyester staple fibre. In a non-limiting example, a bag comprises the superabsorbent polymer polyacrylate. As another non-limiting example, a bag comprises the superabsorbent polymer Needlefelt type 0570N700400 (Technical Absorbents). In some cases, a bag comprises two or more materials with absorbing properties. In some cases, a bag comprises a mixture of super absorbent polymer and cellulose fibers.

In some embodiments, an absorbent material is in a powder or granular form within a bag. In some embodiments, an absorbent material is enclosed within a casing within the bag. In some embodiments, the absorbent material comprises a superabsorbent polymer. The casing is sometimes referred to as a transmissive material or layer which allows fluid to flow into the casing to the absorbent material, while retaining the absorbent material within the casing. In some cases, the transmissive material has a wicking property, where fluid transfer into the casing is facilitated by the wicking property of the transmissive material, for example, via capillary action. In other or additional cases, a separate and/or additional wicking layer is provided on an exterior of the casing to draw liquid into the casing to the absorbing material. In some cases, a layer of the transmissive material enclosing the absorbent material is between about 0.02 mm and 0.2 mm thick or between about 0.08 mm and 0.15 mm thick. Non-limiting examples of transmissive materials include non-woven polypropylene, cellulose fibres, non-woven HDPE and a combination thereof.

In some embodiments, a load-bearing component comprises one or more pillars that resist compression of a bag under a compression pressure of about 75 to about 125 mmHg, wherein the bag does not compress to a height smaller than 90% of the height of the bag prior to application of the compression pressure. In various aspects, a pillar material is flexible, tough, resistance to fatigue, mouldable, or any combination thereof. Non-limiting examples of pillar materials include polypropylene, high-density polyethylene, polyoxymethylene, polyethylene terephthalate, acrylonitrile butadiene styrene, and nylon. Pillar heights may be selected according to the size of the bag such that the bag is configured to contain a desired volume of liquid. In some cases, a pillar has a height between about 1.5 cm and about 5 cm, or at least about 1 cm, 2 cm, or 3 cm.

Wicking Material

In some aspects of the disclosure, a bag for fluid collection provided herein comprises a wicking material. Wicking materials include materials configured to receive liquid and then rapidly transport the liquid, for example, via capillary action, to another material adjacent the wicking material. For instance, the wicking material receives liquid drawn into the bag and then transfers the liquid to the absorbent material within the bag, where the absorbent material absorbs and retains the liquid. In some embodiments, a wicking material wicks more than 15 mm of water vertically over a time period of 24 hours. In some cases, the absorbent material is a superabsorbent polymer. In exemplary embodiments, a bag for fluid collection provided herein comprises a wicking material positioned adjacent an absorbent material described herein. Non-limiting examples of wicking materials include cellulose pulp, cotton, tissue paper, non-woven polyester, and a combination thereof. In some configurations, about a 0.05-10 mm, or about a 0.2-2 mm layer of wicking material is positioned adjacent to an absorbent material.

Air Passageway

In some aspects of the disclosure, a bag for fluid collection provided herein comprises an air passageway defined by an air passageway structure within the interior of the bag. In exemplary embodiments, the air passageway structure is a three-dimensional hydrophobic structure configured to maintain the air passageway open under pressure. For some cases where the bag comprises an expandable absorbent material, the air passageway structure maintains the air passageway open against the expanding absorbent material. In some cases, the structure ensures a low pressure drop for air at expected flow rates, for instance, flow rates between 10 ml/hour and 300 ml/min. In some embodiments, the air passageway structure comprises gauze, reticulated polyurethane foam, layered netting, a Velcro or a combination thereof. In some embodiments, a layer of the air passageway structure is provided within the bag providing an air passageway with a diameter of about 1-10 mm. The air passageway structure is positioned in the bag at any location that allows for passage of air between a first opening and second opening of the bag. In some cases, the air passageway is positioned within a center of a bag, surrounded by a wicking and/or absorbing material configured to receive liquid while the air is continues through to the second opening of the bag.

Fluid Collection Apparatus

In some aspects of the disclosure, a bag for collecting fluid is at least partially covered at its exterior and/or positioned adjacent to a structural body. In some embodiments, the body comprises an inlet and an outlet, wherein the inlet is configured to be in fluid communication with a fluid to be drawn in to the bag and the outlet is configured to be in fluid communication with a source of negative pressure. In some configurations, the inlet and the outlet are positioned within a single attachment point or port within the body. In some cases, the first opening and the second opening of the bag are positioned within a single region of the bag and the first opening is configured to be in fluid communication with the inlet of the body positioned adjacent the bag, and the second opening is configured to be in fluid communication with the outlet of the body. In such a configuration, when the fluid collection apparatus is used in a NPWT application, the port allows for ease of fluid connection to a dressing and negative pressure source.

In some cases where a bag is adjacent to a body, the body covers an exterior side of the bag. As a non-limiting example, the body covers a first side comprising the single region of the bag comprising the first and second openings. In some cases, the body covers 1, 2, 3, 4, 5, or 6 sides of a bag. Covering a side of a bag includes covering a portion of a side of a bag. For example, in some instances a body comprises one or more openings or viewing windows, and one or more sides of the bag are not fully covered by the body corresponding to the one or more openings or viewing windows.

Exemplary body materials include materials suitable for supporting a port or attachment point to a source of fluid and a source of negative pressure, for example, a plastic material. In some embodiments, the body comprises a material having a stiffness between about 0.1 and about 10 GPa. The body need not cover an entire side or bag, so long as the body supports an attachment point for connecting with the fluid source and/or negative pressure source.

In some embodiments, a bag for collecting fluid is at least partially covered by a panel. In some embodiments, the bag is covered at one or more sides by a body and at one or more sides by a panel. As a non-limiting example, for a bag having six sides, a first side of the bag is covered by a body, a second side opposite the first side is covered by the panel, and the four remaining sides are covered partially by a combination of the body and the panel, wherein the body and the panel are connected at the four remaining sides. As another non-limiting example, for a bag having six sides, a first side of the bag is covered by a body and the five remaining sides are covered by the panel, or vice versa. In some cases, a panel comprises a fabric material. An exemplary fabric would be soft to the touch, woven, hydrophobic, elastic and/or heat weldable, e.g., a woven polypropylene.

In some embodiments, provided herein is a fluid collection apparatus comprising a bag for collecting fluid as described herein, and a body and/or panel covering at least a portion of the bag. In some embodiments, a fluid collection apparatus has a height less than about 5, 4, 3, 2, 1, or 0.5 cm prior to collection of fluid. In some embodiments, a fluid collection apparatus has a height of about 0.5-5 cm, 0.5-4 cm, 0.5-3 cm, or 0.5-2 cm prior to collection of fluid. For a fluid collection apparatus comprising an expandable bag, in some cases the height of the fluid collection apparatus when the bag is in the non-expanded state is less than about 5, 4, 3, 2 or 1 cm, or about 0.5-5 cm, 0.5-4 cm, 0.5-3 cm, or 0.5-2 cm. For a fluid collection apparatus comprising an expandable bag, in some cases the height of the fluid collection apparatus when the bag is in the fully expanded state is greater than about 1, 2, 3, 4, 5, 6, 7 or 8 cm, or about 1-8 cm, 2-8 cm, 2-6 cm, or 2-6 cm. In some embodiments, an expandable bag comprising an absorbing material has an aspect ratio from about 1:1 to about 10:1, where the aspect ratio is a ratio of the smallest dimension of the bag to the largest dimension of the bag. For a bag having a non-absorbing load-bearing component, such as a plurality of pillars, the height of the bag is maintained around the same height before application of negative pressure, during negative pressure application and prior to liquid intake, and during liquid intake and retention in the bag. Non-limiting examples of bag heights having such non-absorbing load-bearing components include between about 1 cm and about 5 cm. In some cases, a bag having a non-absorbing load-bearing component has an internal volume or about 300 ml. In some cases, the aspect ratio of a bag comprising a non-absorbing load-bearing material has an aspect ratio between about 1:1 and about 2:1. In some cases, the weight of the fluid collection apparatus is between about 40 and about 400 g or between about 80 g and about 200 g, prior to the retention of fluid. This weight is inclusive of the bag and any liquid retaining materials or other elements within the bag and/or outside of the bag, for example, transmission and wicking layers and/or cover(s).

In some embodiments, a body is supplied separate from a bag in a fluid collection apparatus. In some cases, a plurality of bags may be stacked together for storage and a plurality of bodies may be stacked together for storage. This may reduce the footprint of the apparatus in storage. In some implementations, a bag is a disposable portion of a fluid collection apparatus and the body is reusable for a given patient and/or number of bag changes.

Systems and Kits

In one aspect of the disclosure, provided herein are systems comprising a bag or fluid collection apparatus described herein and one or more accessory elements. Accessory elements include materials useful for performing a negative pressure therapy such as NPWT. In some embodiments, an accessory comprises a wound dressing. A wound dressing includes, without limitation, a dressing having a cover for sealing around a wound site and maintaining a negative pressure environment at the wound site, where the cover further comprises an adhesive for the sealing and an opening for the transfer of negative pressure. Non-limiting examples of wound dressing covers include polyurethane films having, for example, a polyurethane adhesive. In some embodiments, an accessory comprises a source of negative pressure. Sources of negative pressure include pumps configured to maintain a negative pressure between about 75 mmHg and about 125 mmHg below atmospheric pressure. In exemplary embodiments, a pump is a diaphragm pump. Additional accessory items include one or more conduits or tubings configured to connect the bag and/or fluid collection apparatus to a source of negative pressure and/or wound dressing; and a connector configured to connect the outlet of the apparatus to a source of negative pressure, and connect the inlet of the apparatus to the wound dressing.

Methods

In one aspect of the disclosure, provided herein are methods for collecting fluid using a bag and/or fluid collection apparatus described herein. In some embodiments, a method for collecting fluid employs a fluid collection apparatus comprising an expandable bag having first opening and a second opening, the interior of the expandable bag comprising an absorbent material, and a pathway connecting the first opening and the second opening; wherein the pathway has a plurality of openings and the length of the pathway is greater than the length of the expandable bag. The method comprises providing a first fluid connection between the first opening and the fluid to be collected, and providing a second connection between the second opening and a source of negative pressure, and then applying the source of negative pressure to draw the fluid into the bag. As the fluid is drawn into the bag, it is released through the plurality of openings in the pathway to be absorbed by the absorbent material. The bag expands with the absorption of the fluid. In some cases, the expandable bag is viewable through a covering, such as a body and/or panel, positioned adjacent the bag such that a user may view the collection of the fluid. In some cases, the method further comprises viewing collection of the fluid and then changing the bag when the bag has retained a given amount of fluid. For instances where the fluid collection apparatus comprises a body, the body may comprise an inlet corresponding to the first opening of the bag and an outlet corresponding to the second opening of the bag, wherein the inlet and outlet are in communication with the fluid to be collected and the source of negative pressure, respectively.

In some embodiments, provided herein are negative pressure wound therapy (NPWT) methods for collecting fluid from a wound site of a patient in need thereof using a fluid collection apparatus as described herein. In some embodiments, the fluid collection apparatus comprises an expandable bag having first opening and a second opening, the interior of the expandable bag comprising an absorbent material, and a pathway connecting the first opening and the second opening; wherein the pathway has a plurality of openings and the length of the pathway is greater than the length of the expandable bag. The NPWT method comprises positioning a wound dressing over the wound site so that the region between the wound dressing and the wound site is in fluid communication with the first opening of the fluid collection apparatus. The NPWT method further comprises providing a source of negative pressure that is in fluid communication with the second opening of the fluid collection apparatus. Once the fluid collection apparatus is connected to the wound dressing and the source of negative pressure, the method comprises applying a negative pressure from the source of negative pressure to the wound site via the fluid collection apparatus to draw fluid from the wound site, through the first opening of the expandable bag, and along the pathway; wherein the fluid is drawn through the plurality of openings of the pathway to the absorbent material as the fluid is drawn along the pathway; and absorbing the fluid in the absorbent material; wherein the expandable bag expands during absorption. In some embodiments, the fluid collection apparatus is positioned next to the patient in an orientation-independent manner. This orientation independence may be due to the fluid pathway of the bag, which directs fluid through the bag without dependence of the orientation of the bag.

In some embodiments, the negative pressure applied from the negative pressure source is between about 75 mmHg and about 125 mmHg below atmospheric pressure.

In some embodiments, as the fluid is drawn through the openings of the fluid pathway, the fluid distributes evenly within a section of absorbent material. For example, in cases wherein a bag comprises an absorbent material that expands upon absorption, a first height of an expanded absorbent material is not more than 20%, 35%, 50%, or 75% greater than a second height of the expanded absorbent material measured within the same section of the bag and within the same axes. Then as time passes, the fluid may diffuse to other sections of the bag. In some embodiments, a bag is divisible into 2, 3, 4, 5, 6, 7, 8, 9, or 10 sections. In some cases, the sections are about equal in length and/or width. In some cases, this fluid distribution within a section is aided by a wicking material positioned within the bag, wherein the wicking material transfers fluid from the fluid pathway to the absorbent material.

A non-limiting embodiment of a fluid collection apparatus used in the methods described herein generally comprises a flexible bag having a load-bearing material which withstands application of negative pressure while retaining fluid drawn into the bag. The flexibility of the bag may be evaluated by a number of parameters, including stiffness, non-elastic strain, plastic deformation, bending angles upon application of forces F and R, as well as subjective parameters such as perceived flexibility by touch. In some cases, the bag has a stiffness between about 1.5 MPa and about 1 GPa. Stiffness, non-elastic strain, plastic deformation can all be characterized using a tensometer as described in relationship to measure fracture strain and force displacement above. By logging the force and displacement during both loading and unloading the sample, the inspection of the plotted data allow determination of the plastic deformation, non-elastic strain and the stiffness is obtained from the measured load and displacement and related to the cross sectional area of the sample under test. Bending angles under applied loads can be assessed by applying a load to a sample to impose a bend on the material and by using an instrument such as a shadowgraph e.g., the DP Digital Profile Projector or PV300 Standard Profile Projector as supplied by Spectrum Metrology Ltd, 8 Ireton Avenue, Leicester, where bend angles under a range of conditions can be measured. In various embodiments, a flexible bag is comprised of PVC, multi layered laminate, or more generally, a plastic film optionally having a barrier property. In some embodiments, the bag is plastically deformable, having a first deformation angle of θ1 under application of forces F and R, which decreases by no more than about 20% to angle θ2 when the forces F and R are removed. In some embodiments, a layer of the bag has a thickness between about 0.01 mm and about 0.5 mm. In some embodiments, a thickness of a bag comprising an absorbing material is less than about 20 mm. In some embodiments, the bag comprises an absorbent material, for example, one that expands upon fluid absorption, including a superabsorbent that absorbs between about 4 and 10 times its weight in saline liquid. In some embodiments, liquid drawn into the bag using the methods described herein is drawn along a pathway in a transmission layer, through a plurality of openings in the transmission layer, and into an adjacent absorbing material, optionally via a wicking layer.

In some embodiments, upon application of the negative pressure, the expandable bag does not collapse to a height less than about 90% of the height of the expandable bag prior to application of the negative pressure. In some cases, as the fluid is drawn into the expandable bag, the expandable bag expands to a height greater than the height of the bag in the non-expanded state.

In some embodiments of the method, the patient applies a compression pressure to the fluid collection apparatus and/or bag thereof, of about 10 to about 100 mmHg for between about 1 and about 60 min, where this pressure is in addition to an applied negative pressure during therapy. In some such cases, the fluid collection apparatus and/or bag thereof retains at least about 80% of the absorbed fluid during compression.

In another aspect of the disclosure, provided herein is a method of manufacturing a fluid collection apparatus, the method comprising: (a) positioning a first bag outer layer in a nest, with a first side of the first bag outer layer facing the nest and a second side of the first bag outer layer facing away from the nest, the second side of the first bag outer layer having a first perimeter comprising a first seam; (b) positioning an inlet tube, an outlet tube, and one or more inner layers adjacent to the second side of the first bag outer layer and within the first perimeter; (c) covering the inlet tube, outlet tube, and the one or more inner layers with a second bag outer layer, wherein the second bag outer layer comprises a first opening positioned adjacent the inlet tube, and a second opening positioned adjacent the outlet tube; and wherein a first side of the second bag outer layer has a second perimeter comprising a second seam, and the first side faces the first bag outer layer; and (d) sealing the first seam and the second seam to enclose the inlet tube, the outlet tube, and the one or more inner layers within the first bag outer layer and second bag outer layer. Non-limiting examples of sealing methods include heat and RF welding. In some embodiments, the method further comprises joining the bag with a rigid or semi-rigid covering, for example, by welding, adhesives or mechanical trapping. In some embodiments, the one or more inner layers comprise a load-bearing component and a transmission layer defining a fluid pathway between the inlet tube and the outlet tube, and thus the first opening and second opening, respectively. In some cases, the load-bearing component is an absorbing material. In some cases, the one or more inner layers comprise a wicking layer. In some cases, the first bag outer layer and the second bag outer layer comprise the same material. For example, the first bag outer layer and second bag outer layer comprise PVC.

EXAMPLES

Example 1: Fluid Collection Apparatus

A fluid collection apparatus was manufactured comprising a flexible bag for collecting and retaining fluid within a superabsorbent polymer positioned within the bag.

The bag was made of polyvinyl chloride (PVC) with a thickness of 0.15 mm. The PVC film has a Young's modulus of 1.25 GPa. Using a tensometer to apply a tensile load to a material sample and by logging the load and displacement the stress and strain can be calculated. The Young's modulus E, can then be calculated by dividing the tensile stress, by the extensional strain, in the elastic portion of the physical stress-strain curve. The bag is configured to hold 275 mL of fluid, and has an absorbing pathway length of 130 mm, a width of 70 mm, and an initial height of 12.5 mm.

The superabsorbent polymer was sodium polyacrylate, in a laminate structure. The superabsorbent polymer was enclosed within a transmissive material such that fluid was able to reach the superabsorbent polymer, but the superabsorbent polymer did not escape from within the enclosure. The transmissive material was 0.1 mm thick spunbond polypropylene non-woven. The total volume of super absorbent laminate used was approximately 115 cm$^3$, corresponding to a weight of approximately 65 g.

Positioned adjacent the superabsorbent laminate, and within the bag was a layer of wicking material comprising a cotton pad of 2 mm thickness.

A first side of the bag comprised a first opening and a second opening. Positioned over the first side was a body comprising a port having an inlet and an outlet. The body was positioned over the bag such that the inlet was adjacent the first opening and the outlet was adjacent the second opening. A second side opposite the first side of the bag was covered by a panel. The other side of the bag was enclosed by the joining of the body and the panel. The body was constructed from PVC with a material stiffness of approximately 3 GPa. The panel was polyester, elastane blend, approximately 80%, 20% respectively.

Positioned within the bag was a transmission layer for distributing fluid drawn into the bag from the inlet, through the transmission layer, to the wicking layer, and then the superabsorbent laminate for absorption. The transmission layer was constructed of two layers of woven high-density polypropylene (HDPE) mesh offset and welded together to form a 3D sheet. The transmission layer has holes 1.6 mm×1.6 mm, with the diameter of the HDPE fibers forming the mesh at approximately 0.25 mm. The thickness of the two sheets was therefore approximately 0.5 mm.

Example 2: Method of Manufacturing

A fluid collection apparatus having a superabsorbent polymer as generally depicted in FIG. 3 was manufactured.

A super absorbent laminate was divided into two portions, and each portion was enclosed in a transmissive material (0.1 mm thick spunbond polypropylene non-woven). The transmissive material was then radio frequency (RF) welded closed around the super absorbent laminate to generate two layers (304).

An upper moulding (307) and lower moulding (302) were plastic moulded from PVC, each comprising an inlet and an outlet.

The components of the bag were placed in a nest in the following order: a lower layer of PVC to serve as a first side of the bag (301), a super absorbent laminate (304), a transmission layer (303) as described in Example 1, a super absorbent laminate (304), tubes (306) corresponding to the inlets and outlets header and lower layers, and upper PVC layer (305) to serve as a second side of the bag. An optional wicking material is added on either side of transmission layer (303) (not shown). In this example, the superabsorbent laminate has wicking properties. The tubes were RF welded. The perimeter of the bag layers (301, 305) were RF welded. Outer material panels were sewn together and the bag placed inside the sewn panels to obscure a view of the bag (not shown). Tubing was pushed into lower moulding (302) at tubes (306). Lower moulding (302) was snapped onto upper moulding (307) to trap both the bag and material panels in place. A general side view of the connection between lower moulding (302) and upper moulding (307) is shown in FIG. 7.

In use, air travels from the wound and passes through the manufactured bag in the following order: upper moulding (307), lower moulding (302), inlet tube at (306), inside of the bag between layers (301) and (305), outlet tube at (306), lower moulding (302), and upper moulding (307). Exudate travels from the wound and into the manufactured bag in the following order: upper moulding (307), lower moulding (302), inlet tube at (306), transmission layer (303), absorbing layers (304). The exudate follows the general circular path (312) from an inlet (309) to an outlet (310) as outlined by the periphery weldings (311) of the bag, as generally shown in FIG. 6. In this example, the path of exudate through the thickness of the super absorbent laminate (304) is not structurally constrained.

Example 3: Collection of Exudates During Negative Pressure Wound Therapy

The fluid collection apparatus of Example 1 was used to collect exudates from a wound during negative pressure wound therapy. The inlet of the apparatus was connected to a wound dressing via a first conduit and the outlet of the apparatus was connected to a source of negative pressure via a second conduit.

The absorbency of the superabsorbent polymer within the fluid collection apparatus was tested under 125 mmHg negative pressure applied at the outlet of the apparatus. Normal saline solution (0.9% wt NaCl) was drawn through the inlet of the apparatus at a rate of 10 mL/hr. A volume of approximately 90 cm$^3$ of superabsorbent polymer absorbed 275 mL of fluid (an absorption of approximately 3 mL/cm$^3$). The thickness of the bag went from approximately 1 cm to approximately 4 cm upon absorption of the 275 mL of fluid.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the inventions described herein may be employed in practicing the inventions. It is intended that the following claims define a scope of the inventions and that methods and structures within the scope of these claims and their equivalents be covered thereby.

What is claimed is:

1. A fluid collection apparatus for negative pressure wound therapy comprising a flexible bag having a first opening for receiving fluid from a wound dressing and a second opening for attachment to a negative pressure source; wherein the bag comprises
    a. a top layer, a bottom layer, a first absorbent layer adjacent to the top layer, a second absorbent layer adjacent to the bottom layer, a transmission layer located between the first absorbent layer and the second absorbent layer, wherein each of the top layer, the bottom layer, the first absorbent layer, the second absorbent layer, and the transmission layer include a hole, and a weld connecting the top layer to the bottom layer, the top layer and bottom layer defining an interior for collection of the fluid and the weld defining, with the top layer and the bottom layer, a circular fluid pathway for the fluid, the circular fluid pathway connecting the first opening and the second opening, wherein the weld directs fluid from the first opening to the second opening through which a negative pressure is applied to draw fluid through the bag;
    b. a load-bearing component, wherein a position of the fluid connection apparatus is orientation independent as a result of the structure defining the circular fluid pathway;
    c. a snap together moulding extending through each of the holes of the top layer, the bottom layer, the first absorbent layer, the second absorbent layer, and the transmission layer, wherein the snap together moulding provides a fluid pathway connecting the first opening and the second opening.

2. The fluid collection apparatus of claim 1, wherein the circular fluid pathway has a length greater than the length of the flexible bag.

3. The fluid collection apparatus of claim 2, wherein the circular fluid pathway has a length at least 20% longer than the length of the flexible bag.

4. The fluid collection apparatus of claim 2, wherein the circular fluid pathway has a length of at least 10 cm.

5. The fluid collection apparatus of claim 1, wherein the circular fluid pathway has a height or diameter from 0.1 mm to 4 mm.

6. The fluid collection apparatus of claim 1, wherein the structure defining the circular fluid pathway comprises a plurality of openings to permit fluid to flow out of the fluid pathway as fluid passes through the apparatus.

7. The fluid collection apparatus of claim 6, wherein the structure defining the circular fluid pathway is a tube connecting the first opening to the second opening.

8. The fluid collection apparatus of claim 6, wherein the structure defining the circular fluid pathway is the transmission layer.

9. The fluid collection apparatus of claim 6, wherein the structure defining the circular fluid pathway is a channel within a section of the flexible bag.

10. The fluid collection apparatus of claim 1, wherein the load-bearing component comprises an absorbent material.

11. The fluid collection apparatus of claim 1, wherein the load-bearing component comprises one or more pillars of non-absorbing load-bearing material that resist compression of the flexible bag under a compression pressure of 10 to 50 mmHg, wherein the flexible bag does not compress to a height smaller than 90% of the height of the flexible bag prior to application of the compression pressure.

12. The fluid collection apparatus of claim 1, further comprising a wicking material, wherein the wicking material transfers fluid from the fluid pathway to the first and second absorbent layers.

13. The fluid collection apparatus of claim 1, further comprising an air passageway defined by a hydrophobic structure within the interior of the flexible bag.

14. The fluid collection apparatus of claim 1, further comprising wherein the transmission layer encloses the load-bearing component within the interior of the flexible bag.

15. The fluid collection apparatus of claim 1, further comprising a filter.

16. A method for collecting fluid from a wound site of a patient, the method comprising:
    a) providing
        i) a fluid collection apparatus comprising an expandable bag including a top layer, a bottom layer, a first absorbent layer adjacent to the top layer, a second absorbent layer adjacent to the bottom layer, a transmission layer located between the first absorbent layer and the second absorbent layer, wherein each of the top layer, the bottom layer, the first absorbent layer, the second absorbent layer, and the transmission layer include a hole, a weld connecting the top layer to the bottom layer, the expandable bag having a first opening and a second opening, and a snap together moulding extending through each of the holes of the top layer, the bottom layer, the first absorbent layer, the second absorbent layer, and the transmission layer, wherein the snap together moulding provides a fluid pathway connecting the first opening and the second opening, the weld defining a circular fluid pathway connecting the first opening and the second opening, wherein the circular fluid pathway has a plurality of openings, and wherein a position of the fluid collection apparatus is orientation independent as a result a structure of the circular fluid pathway;
        ii) a wound dressing positioned over the wound site, the wound dressing in fluid communication with the first opening of the fluid collection apparatus; and iii) a source of negative pressure, the source of negative pressures in fluid communication with the second opening of the fluid collection apparatus;
b) applying a negative pressure from the source of negative pressure to the wound site via the fluid collection apparatus to draw fluid from the wound dressing, through the first opening of the expandable bag, directing the fluid with the weld from the first opening, and along the circular fluid pathway to the second opening; wherein the fluid is drawn through the plurality of openings of the circular fluid pathway to the absorbent material as the fluid is drawn along the circular fluid pathway; and
c) absorbing the fluid in the first and second absorbent layers; wherein the expandable bag expands during absorption.

17. The method of claim 16, wherein the circular fluid pathway has a length greater than the length of the expandable bag.

18. The method of claim 17, wherein the circular fluid pathway has a length at least 20% longer than the length of the expandable bag.

19. The method of claim 17, wherein the circular fluid pathway has a length of at least 10 cm.

20. The method of claim 16, wherein the circular fluid pathway has a height or diameter from 0.1 mm to 4 mm.

* * * * *